(12) United States Patent
Regueiro-Ren et al.

(10) Patent No.: US 9,920,090 B2
(45) Date of Patent: Mar. 20, 2018

(54) BETULINIC ACID DERIVATIVES WITH HIV MATURATION INHIBITORY ACTIVITY

(71) Applicant: ViiV Healthcare UK (No.5) Limited, Brentford, Middlesex (GB)

(72) Inventors: Alicia Regueiro-Ren, Wallingford, CT (US); Animesh Goswami, New Brunswick, NJ (US); Zhiwei Guo, Sammamish, WA (US); Thomas P. Tully, New Brunswick, NJ (US); Jacob Swidorski, Wallingford, CT (US); Zheng Liu, Wallingford, CT (US); Nicholas A. Meanwell, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/313,139

(22) PCT Filed: Jun. 17, 2015

(86) PCT No.: PCT/US2015/036191
§ 371 (c)(1),
(2) Date: Nov. 22, 2016

(87) PCT Pub. No.: WO2015/195776
PCT Pub. Date: Dec. 23, 2015

(65) Prior Publication Data
US 2017/0204133 A1    Jul. 20, 2017

Related U.S. Application Data

(60) Provisional application No. 62/014,212, filed on Jun. 19, 2014.

(51) Int. Cl.
*C07J 63/00*    (2006.01)
*C07J 71/00*    (2006.01)
(52) U.S. Cl.
CPC ........... *C07J 63/008* (2013.01); *C07J 71/001* (2013.01); *C07J 71/0026* (2013.01)
(58) Field of Classification Search
CPC .................................................. C07J 63/008
See application file for complete search history.

(56) References Cited

U.S. PATENT DOCUMENTS 8,748,415 B2 *    6/2014   Regueiro-Ren ........ C07J 63/008
                                                                    514/172

FOREIGN PATENT DOCUMENTS

WO    WO 2012/106188 A1    8/2012

OTHER PUBLICATIONS

HIV Vaccines [online]. Retrieved from the internet on Jul. 6, 2017 URL: <http://www.hiv.gov/hiv-basics/hiv-prevention/potential-future-options/hiv-vaccines>.*
HIV Vaccine: How Close Are We? [online]. Retrieved from the internet on Jul. 6, 2017 URL: <http://www.healthline.com/health/hiv-aids/vaccine-how-close-are-we>.*

* cited by examiner

*Primary Examiner* — Shawquia Jackson
(74) *Attorney, Agent, or Firm* — Robert H. Brink; Edward R. Gimmi; William R. Majarian

(57) ABSTRACT

Compounds having drug and bio-affecting properties, their pharmaceutical compositions and methods of use are set forth. In particular, betulinic acid derivatives that possess unique antiviral activity are provided as HIV maturation inhibitors, as represented by compounds of Formulas I, II and III:

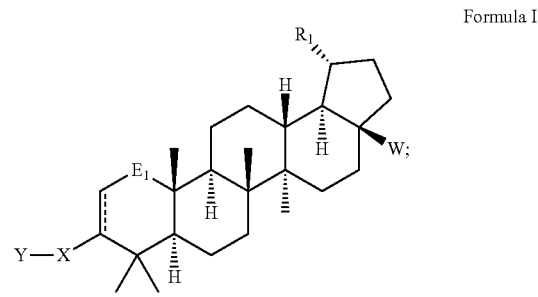

Formula I

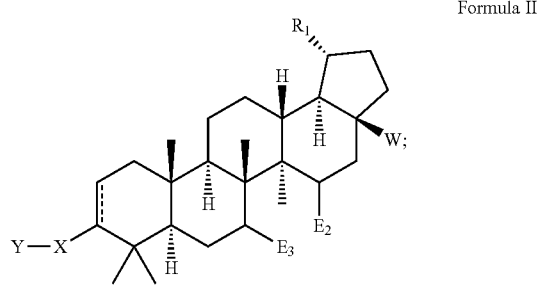

Formula II

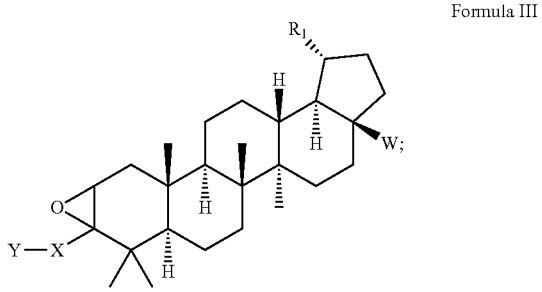

Formula III

These compounds are useful for the treatment of HIV and AIDS.

19 Claims, No Drawings

BETULINIC ACID DERIVATIVES WITH HIV MATURATION INHIBITORY ACTIVITY

CROSS REFERENCE TO RELATED APPLICATION

This application is a § 371 of International Application No. PCT/US2015/036191, filed 17 Jun. 2015, which claims the benefit of U.S. Provisional Application No. 62/014,212, filed 19 Jun. 2014, which are incorporated herein in their entireties.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus −1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains—3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and U.S. Pat. No. 7,745,625 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., "Synthesis of derivatives of plant triterpenes and study of their antiviral and immunostimulating activity," Khimiya y Interesakh Ustoichivogo Razvitiya, Vol. 9, No. 3, pp. 485-491 (2001) (English abstract).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) 1up-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (now U.S. Pat. No. 8,754,068) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (now U.S. Pat. No. 8,802,661).

Reference is also made to the application entitled "C-28 AMINES OF C-3 MODIFIED BETULINIC ACID DERIVATIVES AS HIV MATURATION INHIBITORS" U.S. Ser. No. 13/359,680, filed on Jan. 27, 2012 (now U.S. Pat. No. 8,748,415). In addition, reference is made to the application entitled "C-17 AND C-3 MODIFIED TRITERPENOIDS WITH HIV MATURATION INHIBITORY ACTIVITY" U.S. Ser. No. 13/359,727 filed on Jan. 27, 2012 (now U.S. Pat. No. 8,846,647). Further reference is also made to the application "C-3 CYCLOALKENYL TRITERPENOIDS WITH HIV MATURATION INHIBITORY ACTIVITY" filed U.S. Ser. No. 13/760,726 on Feb. 6, 2013 (now U.S. Pat. No. 8,906,889), as well as to the application entitled "TRITERPENOIDS WITH HIV MATURATION INHIBITORY ACTIVITY" filed U.S. Ser. No. 14/682,179 on Apr. 9, 2015.

What is now needed in the art are new compounds which are useful as HIV maturation inhibitors, as well as new pharmaceutical compositions containing these compounds.

SUMMARY OF THE INVENTION

The present invention provides compounds of Formulas I, II and III below, including pharmaceutically acceptable salts thereof, their pharmaceutical formulations, and their use in patients suffering from or susceptible to a virus such as HIV. The compounds of Formulas I, II and III are effective antiviral agents, particularly as inhibitors of HIV. They are useful for the treatment of HIV and AIDS.

One embodiment of the present invention is directed to a compound, including pharmaceutically acceptable salts thereof, which is selected from the group of:

a compound of formula I

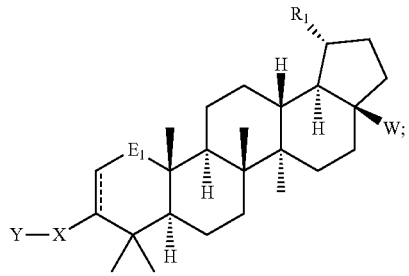

Formula I a compound of formula II

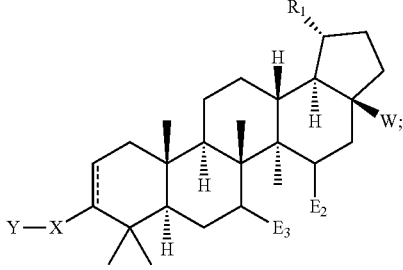

Formula II and a compound of formula III

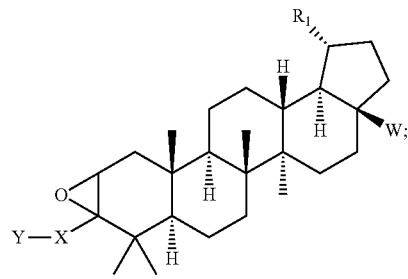

Formula III wherein $R_1$ is isopropenyl or isopropyl;
$E_1$ is selected from the group of —$CHOR_{22}$, —CO, —CHF and —$CF_2$;
$E_2$ and $E_3$ are selected from —$CHOR_{22}$ and F; or
$E_2$ and $E_3$ can together form a ketal:

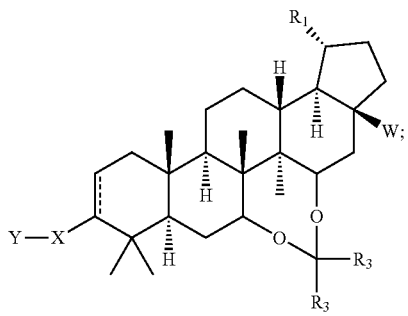

wherein X is selected from the group of phenyl, heteroaryl ring, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl and $C_6$ cyclodialkenyl;
X is substituted with A, wherein A is at least one member selected from the group of —H, -halo, -hydroxyl, —$C_{1-6}$ alkyl, —$C_{1-6}$ alkoxy, —$C_{1-6}$ haloalkyl, —$NR_2R_2$, —$COOR_2$, and —$C(O)NR_2R_2$,
wherein $R_2$ is selected from the group of —H, —$C_{1-6}$ alkyl, -alkylsubstituted $C_{1-6}$ alkyl, and -arylsubstituted $C_{1-6}$ alkyl;
Y is selected from the group of —$COOR_2$, —$C(O)NR_2SO_2R_3$, —$C_{3-6}$ cycloalkyl-$COOR_2$, —$C_{1-6}$ alkyl-$COOR_2$, -alkylsubstituted $C_{1-6}$alkyl-$COOR_2$, —$SO_2NR_2C(O)R_2$, and tetrazole,
$R_3$ is —$C_{1-6}$ alkyl or -alkylsubstituted $C_{1-6}$ alkyl;
W is —$COOR_2$, —$(CH_2)_{0-1}NR_4R_5$, or —$CONR_{20}R_{21}$;
$R_4$ is selected from the group of —H, —$C_{1-6}$ alkyl, —$C_{1-6}$alkyl-$C(OR_3)_2$—$C_{3-6}$cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$alkyl-$C_{3-6}$cycloalkyl-$Q_1$, -aryl, -heteroaryl, substituted heteroaryl, —$COR_6$, —$COCOR_6$, —$SO_2R_7$, and —$SO_2NR_2R_2$,
wherein $Q_1$ is selected from the group of -heteroaryl, substituted heteroaryl, -halogen, —$CF_3$, —$OR_2$, —$COOR_2$, —$NR_8R_9$, —$CONR_{10}R_{11}$ and —$SO_2R_2$;
$R_5$ is selected from the group of —H, —$C_{1-6}$ alkyl, —$C_{3-6}$ cycloalkyl, —$C_{1-6}$ alkylsubstituted alkyl, —$C_{1-6}$alkyl-$NR_8R_9$, —$COR_{10}$, —$COR_6$, —$COCOR_6$, —$SO_2R_7$ and —$SO_2NR_2R_2$;
with the proviso that only one of $R_4$ or $R_5$ can be selected from the group of —$COR_6$, —$COCOR_6$, —$SO_2R_7$ and —$SO_2NR_2R_2$;

$R_6$ is selected from the group of —H, —$C_{1-6}$ alkyl, —$C_{1-6}$ alkyl-substituted alkyl, —$C_{3-6}$ cycloalkyl, —$C_{3-6}$ substituted cycloalkyl-$Q_2$, —$C_{1-6}$ alkyl-$Q_2$, —$C_{1-6}$ alkyl-substituted-alkyl-$Q_2$, —$C_{3-6}$ cycloalkyl-$Q_2$, aryl-$Q_2$, —$NR_{13}R_{14}$, and —$OR_{15}$;

wherein $Q_2$ is selected from the group of -aryl, -heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —$C_{1-6}$ alkyl, —$C_{1-6}$ substituted alkyl, —$C_{3-6}$ cycloalkyl, aryl, and -heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, or $R_8$ and $R_9$ are taken together with the adjacent N to form a cycle selected from the group of:

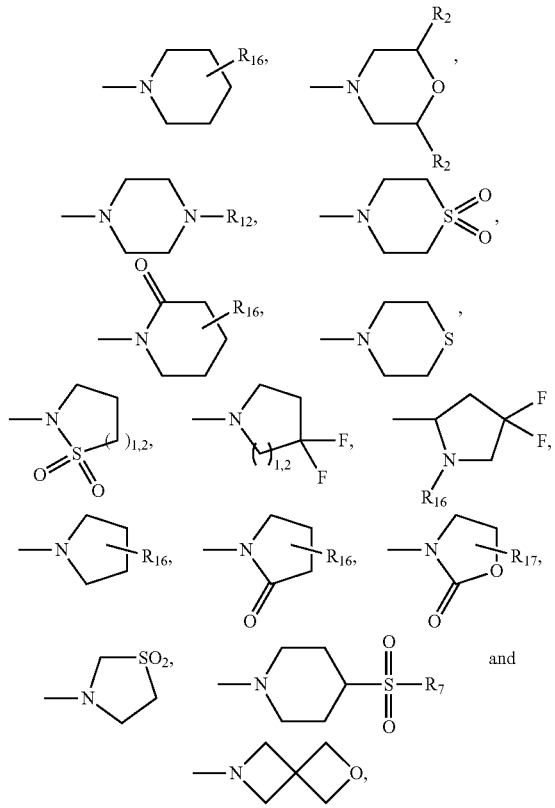

with the proviso that only one of $R_8$ or $R_9$ can be —$COOR_3$;

$R_{10}$ and $R_{11}$ are independently selected from the group of —H, —$C_{1-6}$ alkyl, —$C_{1-6}$ substituted alkyl and —$C_{3-6}$ cycloalkyl;

$R_{12}$ is selected from the group of —$C_{1-6}$ alkyl, —$C_{1-6}$ alkyl-OH; —$C_{1-6}$ alkyl, —$C_{1-6}$ substituted alkyl, —$C_{3-6}$ cycloalkyl, and —$COR_7$;

$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$, and $C_{1-6}$ substituted alkyl-$Q_3$;

$Q_3$ is selected from the group of -heteroaryl, substituted heteroaryl, —$NR_{18}R_{19}$, —$CONR_2R_2$, —$COOR_2$, —$OR_2$, and —$SO_2R_3$;

$R_{15}$ is selected from the group of —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$ and —$C_{1-6}$ substituted alkyl-$Q_3$;

$R_{16}$ is selected from the group of —H, —$C_{1-6}$ alkyl, —$NR_2R_2$, and —$COOR_3$;

$R_{17}$ is selected from the group of —H, —$C_{1-6}$ alkyl, —$COOR_3$, and -aryl;

$R_{18}$ and $R_{19}$ are independently selected from the group of —H, —$C_{1-6}$ alkyl, —$C_{1-6}$ substituted alkyl, —$C_{1-6}$ substituted alkyl-$OR_2$, and —$COR_3$;

$R_{20}$ and $R_{21}$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, or $R_{20}$ and $R_{21}$ are taken together with the adjacent N to form a cycle selected from the group of:

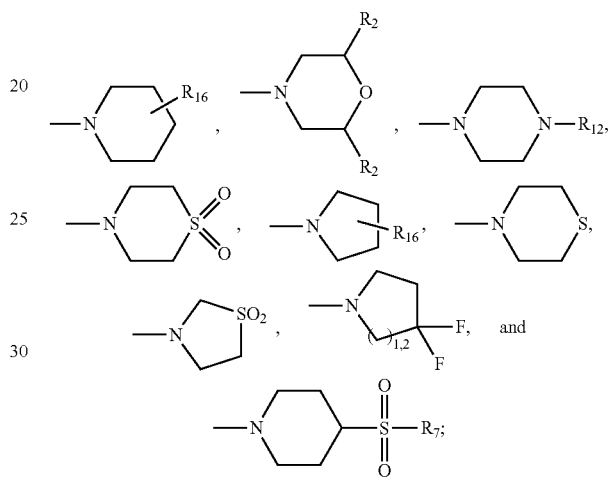

and $R_{22}$ is selected from H and —$COR_3$.

In a further embodiment, there is provided a method for treating mammals infected with a virus, especially wherein said virus is HIV, comprising administering to said mammal an antiviral effective amount of a compound which is selected from the group of compounds of Formulas I, II and III, and one or more pharmaceutically acceptable carriers, excipients or diluents. Optionally, the compound of Formulas I, II and III can be administered in combination with an antiviral effective amount of another-AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising one or more compounds of Formulas I, II, and III, and one or more pharmaceutically acceptable carriers, excipients, and/or diluents; and optionally in combination with another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formulas I, II, and III herein.

Also provided herein are intermediate compounds useful in making the compounds of Formulas I, II and III herein.

The present invention is directed to these, as well as other important ends, hereinafter described.

DETAILED DESCRIPTION OF THE EMBODIMENTS

As used herein, the singular forms "a", "an", and "the" include plural reference unless the context clearly dictates otherwise.

Since the compounds of the present invention may possess asymmetric centers and therefore occur as mixtures of diastereomers, the present disclosure includes the individual diastereoisomeric forms of the compounds of Formulas I, II and III in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" or "halo" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group(s) are preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and its S oxides and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z as defined above and R$^x$ being H or (C$_{1-6}$)alkyl.

A "sulfinyl" group refers to a —S(=O)—R" group, with R" being (C$_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^X$R$^Y$, with R$^X$ and R$^Y$ independently being H or (C$_{1-6}$)alkyl.

A "N-sulfonamido" group refers to a R"S(=O)$_2$NR$_x$— group, with R$_x$ being H or (C$_{1-6}$)alkyl.

A "O-carbamyl" group refers to a —OC(=O)NR$^x$R$^y$ group, with R$^X$ and R$^Y$ independently being H or (C$_{1-6}$)alkyl.

A "N-carbamyl" group refers to a R$^x$OC(=O)NR$^y$ group, with R$^x$ and R$^y$ independently being H or (C$_{1-6}$)alkyl.

A "O-thiocarbamyl" group refers to a —OC(=S)NR$^x$R$^y$ group, with R$^x$ and R$^y$ independently being H or (C$_{1-6}$)alkyl.

A "N-thiocarbamyl" group refers to a R$^x$OC(=S)NR$^y$— group, with R$^x$ and R$^y$ independently being H or (C$_{1-6}$)alkyl.

An "amino" group refers to an —NH$_2$ group.

A "C-amido" group refers to a —C(=O)NR$^x$R$^y$ group, with R$^x$ and R$^y$ independently being H or (C$_{1-6}$)alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$)alkyl.

A "guanidino" group refers to a —R$^x$NC(=N)NR$^y$R$^{y2}$ group, with R$^x$, R$^y$, and R$^{y2}$ independently being H or (C$_{1-6}$)alkyl.

A "amidino" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$)alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

A "4, 5, or 6 membered ring cyclic N-lactam" group refers to

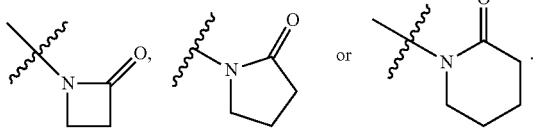

A "spiro" group is a bicyclic organic group with rings connected through just one atom. The rings can be different in nature or identical. The connecting atom is also called the spiroatom, most often a quaternary carbon ("spiro carbon").

An "oxospiro" or "oxaspiro" group is a spiro group having an oxygen contained within the bicyclic ring structure. A "dioxospiro" or "dioxaspiro" group has two oxygens within the bicyclic ring structure.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

As set forth above, the invention is directed to a compound, including pharmaceutically acceptable salts thereof, which is selected from the group of:
a compound of formula I

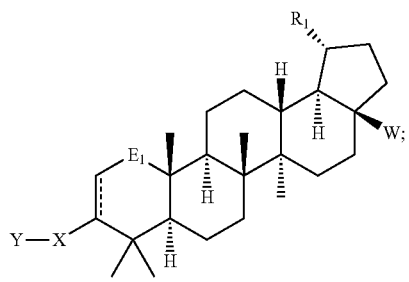

Formula I a compound of formula II

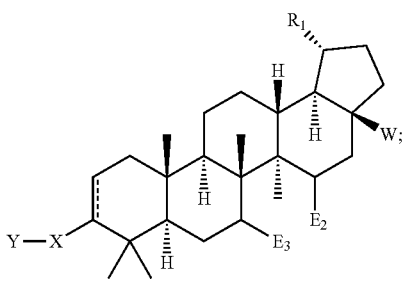

Formula II and a compound of formula III

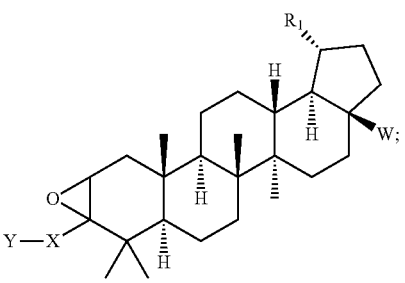

Formula III wherein $R_1$ is isopropenyl or isopropyl;
$E_1$ is selected from the group of —CHOR$_{22}$, —CO, —CHF and —CF$_2$;

$E_2$ and $E_3$ are selected from —CHOR$_{22}$ and F; or
$E_2$ and $E_3$ can together form a ketal:

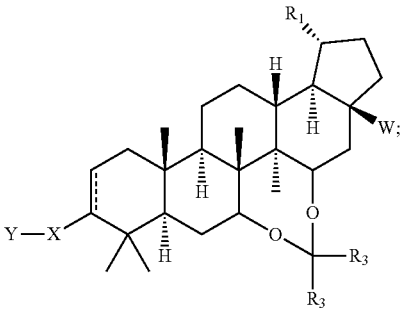

wherein X is selected from the group of phenyl, heteroaryl ring, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl and $C_6$ cyclodialkenyl;

X is substituted with A, wherein A is at least one member selected from the group of —H, -halo, -hydroxyl, —$C_{1-6}$ alkyl, —$C_{1-6}$ alkoxy, —$C_{1-6}$ haloalkyl, —NR$_2$R$_2$, —COOR$_2$, and —C(O)NR$_2$R$_2$, wherein $R_2$ is selected from the group of —H, —$C_{1-6}$ alkyl, -alkylsubstituted $C_{1-6}$ alkyl, and -arylsubstituted $C_{1-6}$ alkyl;

Y is selected from the group of —COOR$_2$, —C(O)NR$_2$SO$_2$R$_3$, —$C_{3-6}$ cycloalkyl-COOR$_2$, —$C_{1-6}$ alkyl-COOR$_2$, -alkylsubstituted $C_{1-6}$alkyl-COOR$_2$, —SO$_2$NR$_2$C(O)R$_2$, and tetrazole, $R_3$ is —$C_{1-6}$ alkyl or -alkylsubstituted $C_{1-6}$ alkyl;

W is —COOR$_2$, —(CH$_2$)$_{0-4}$NR$_4$R$_5$, or —CONR$_{20}$R$_{21}$;

$R_4$ is selected from the group of —H, —$C_{1-6}$ alkyl, —$C_{1-6}$alkyl-C(OR$_3$)$_2$—$C_{3-6}$cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, -aryl, -heteroaryl, substituted heteroaryl, —COR$_6$, —COCOR$_6$, —SO$_2$R$_7$, and —SO$_2$NR$_2$R$_2$, wherein $Q_1$ is selected from the group of -heteroaryl, substituted heteroaryl, -halogen, —CF$_3$, —OR$_2$, —COOR$_2$, —NR$_8$R$_9$, —CONR$_{10}$R$_{11}$ and —SO$_2$R$_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-NR$_8$R$_9$, —COR$_{10}$, —COR$_6$, —COCOR$_6$, —SO$_2$R$_7$ and —SO$_2$NR$_2$R$_2$;

with the proviso that only one of $R_4$ or $R_5$ can be selected from the group of —COR$_6$, —COCOR$_6$, —SO$_2$R$_7$ and —SO$_2$NR$_2$R$_2$;

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substituted-alkyl-$Q_2$, —$C_{3-6}$ cycloalkyl-$Q_2$, aryl-$Q_2$, —NR$_{13}$R$_{14}$, and —OR$_{15}$;

wherein $Q_2$ is selected from the group of -aryl, -heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

$R_7$ is selected from the group of —$C_{1-6}$ alkyl, —$C_{1-6}$ substituted alkyl, —$C_{3-6}$ cycloalkyl, aryl, and -heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —COOR$_3$, or $R_8$ and $R_9$ are taken together with the adjacent N to form a cycle selected from the group of:

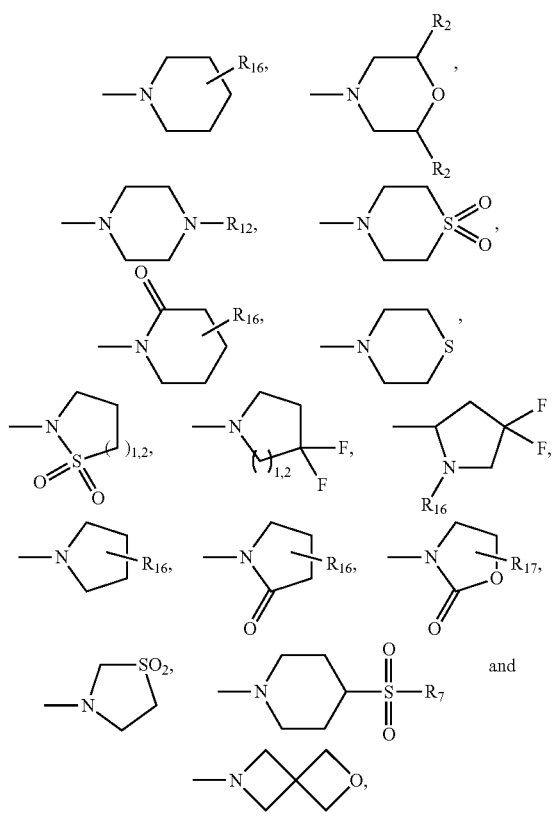

with the proviso that only one of $R_8$ or $R_9$ can be —$COOR_3$;

$R_{10}$ and $R_{11}$ are independently selected from the group of —H, —$C_{1-6}$ alkyl, —$C_{1-6}$ substituted alkyl and —$C_{3-6}$ cycloalkyl;

$R_{12}$ is selected from the group of —$C_{1-6}$ alkyl, —$C_{1-6}$ alkyl-OH; —$C_{1-6}$ alkyl, —$C_{1-6}$ substituted alkyl, —$C_{3-6}$ cycloalkyl, and —$COR_7$;

$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$, and $C_{1-6}$ substituted alkyl-$Q_3$;

$Q_3$ is selected from the group of -heteroaryl, substituted heteroaryl, —$NR_{18}R_{19}$, —$CONR_2R_2$, —$COOR_2$, —$OR_2$, and —$SO_2R_3$;

$R_{15}$ is selected from the group of —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$ and —$C_{1-6}$ substituted alkyl-$Q_3$;

$R_{16}$ is selected from the group of —H, —$C_{1-6}$ alkyl, —$NR_2R_2$, and —$COOR_3$;

$R_{17}$ is selected from the group of —H, —$C_{1-6}$ alkyl, —$COOR_3$, and -aryl;

$R_{18}$ and $R_{19}$ are independently selected from the group of —H, —$C_{1-6}$ alkyl, —$C_{1-6}$ substituted alkyl, —$C_{1-6}$ substituted alkyl-$OR_2$, and —$COR_3$;

$R_{20}$ and $R_{21}$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, or $R_{20}$ and $R_{21}$ are taken together with the adjacent N to form a cycle selected from the group of:

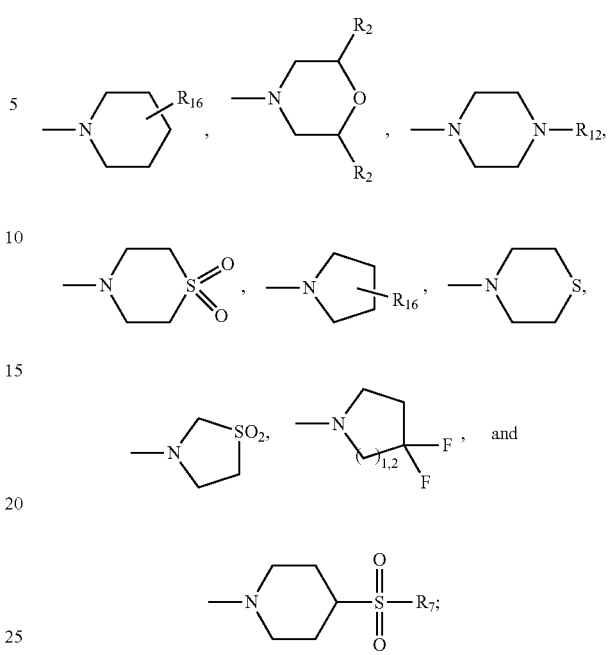

and $R_{22}$ is selected from H and —$COR_3$.

More preferred compounds include those wherein $R_1$ is isopropenyl.

Also preferred are compounds wherein X is phenyl. It is also preferred that Y is —COOH.

In certain embodiments, it is preferred that the compound of the invention has the Formula I. In these embodiments, it is also preferred that $E_1$ is —$CHOR_{22}$. More preferably, $E_1$ is —CHOH or is —CO or is —CHF.

In certain embodiments, it is preferred that the compound of the invention has the Formula II. In these embodiments, it is preferred that $E_2$ and $E_3$ are each —$CHOR_{22}$. It is also preferred that $E_2$ and $E_3$ together form a ketal. Also preferred is the embodiment wherein $R_3$ is methyl.

In certain embodiments, it is preferred that the compound of the invention has the Formula III. In these embodiments, it is also preferred that W is —$(CH_2)_{0-1}NR_4R_5$.

Preferred compounds, including pharmaceutically acceptable salts thereof, as part of the invention including the following:

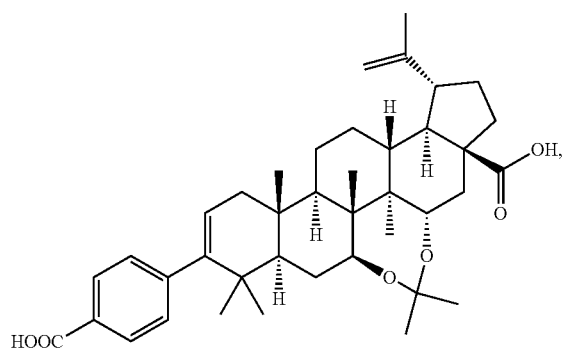

15
-continued
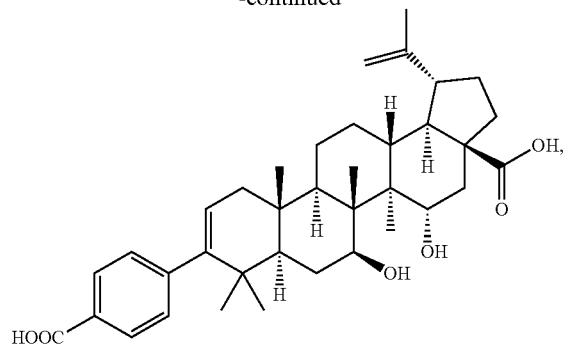
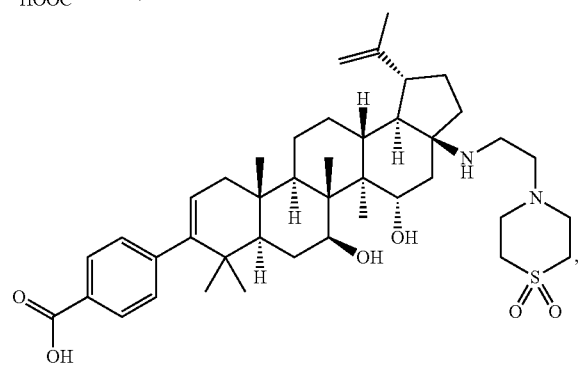
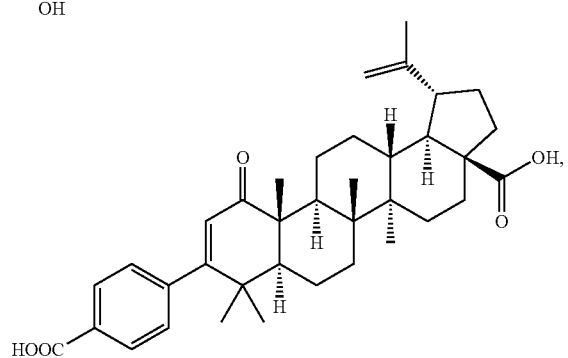
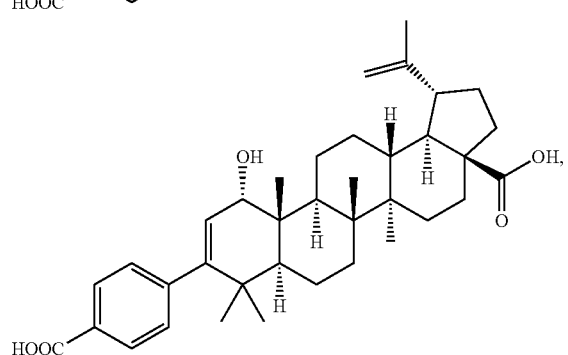
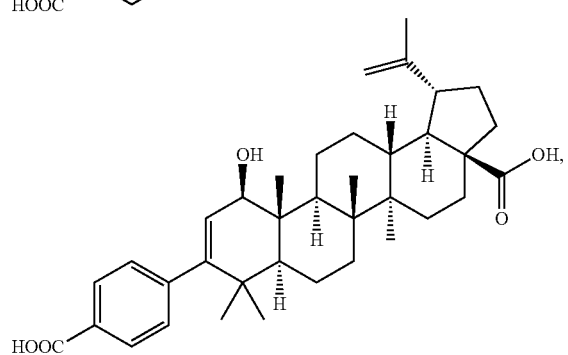
16
-continued
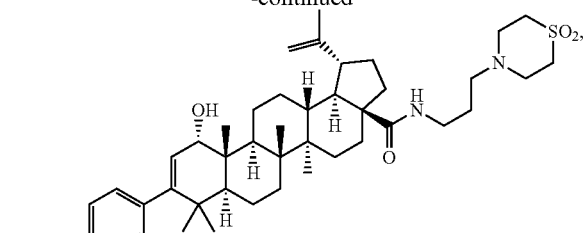
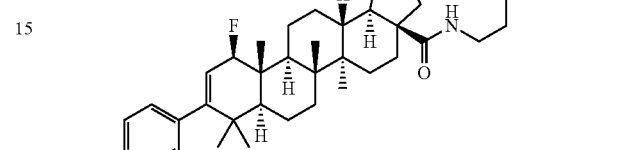
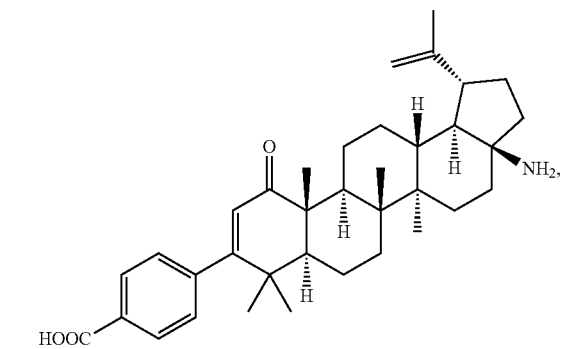
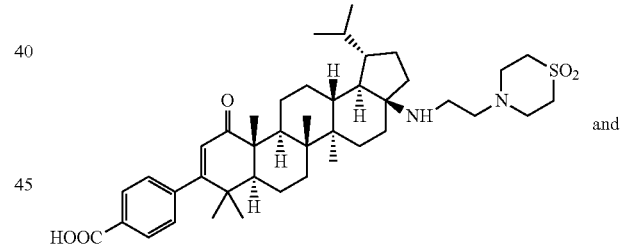
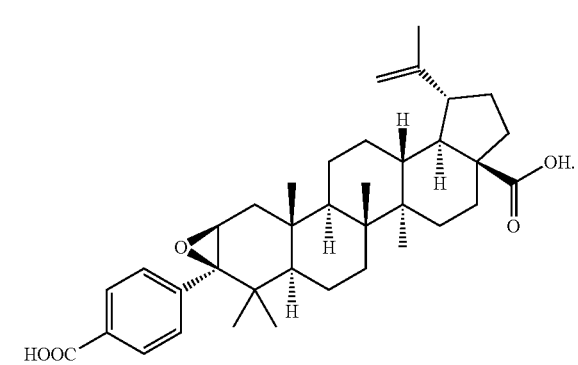
Preferred compounds, including pharmaceutically acceptable salts thereof, as part of the invention also include the following:

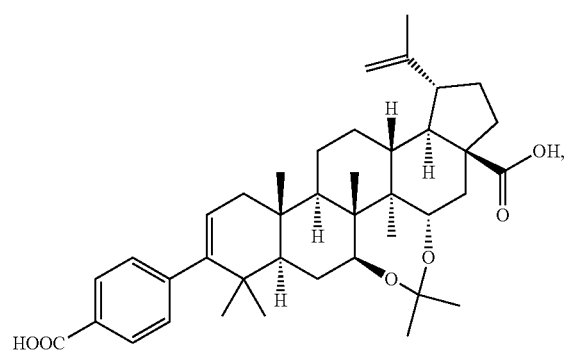

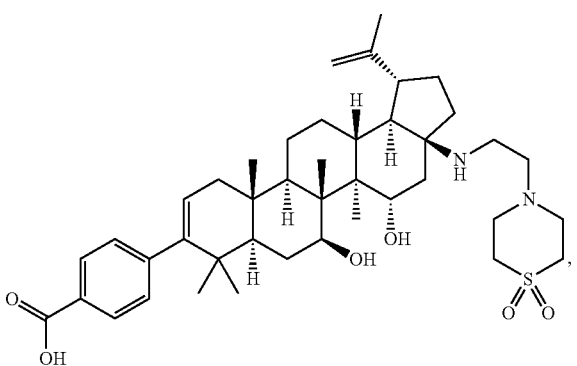

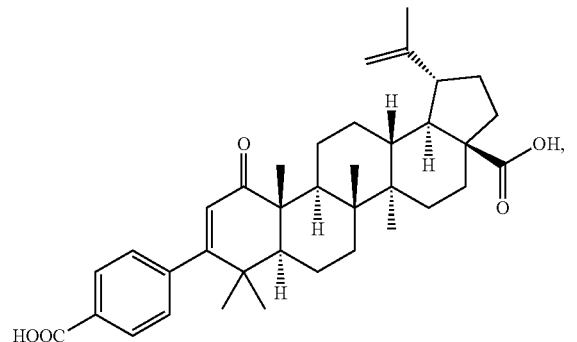

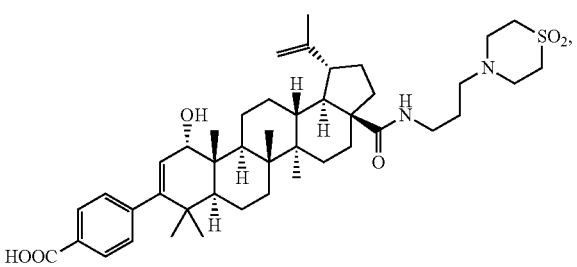

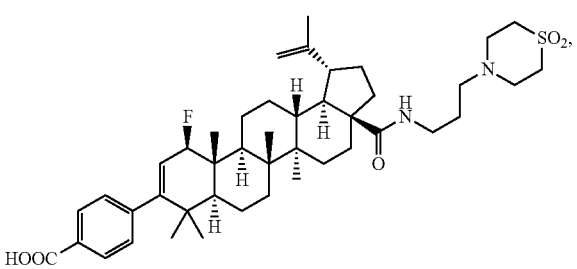

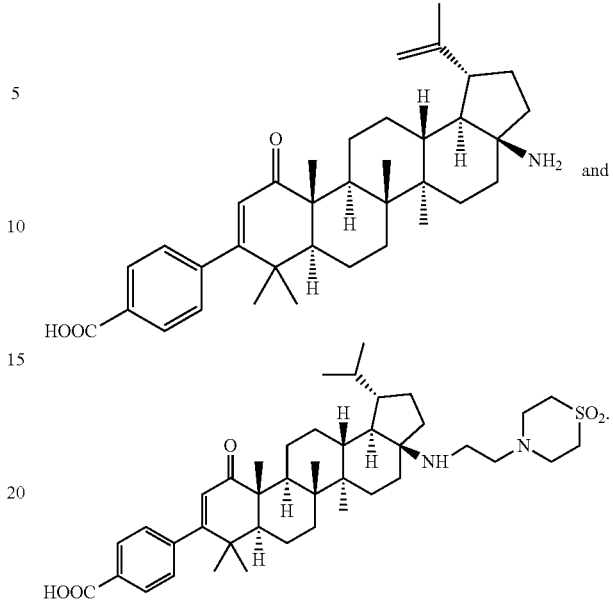

The compounds above represent the mixture of diastereoisomers, and the two individual disastereomers. In certain embodiments, one of the specific diastereomers may be particularly preferred.

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I, II, and III together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, inhibiting, ameliorating and/or healing diseases and conditions associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I, II and III herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |

-continued

| Drug Name | Manufacturer | Indication |
|---|---|---|
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |

-continued

| Drug Name | Manufacturer | Indication |
|---|---|---|
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| Trizivir ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |

-continued

| Drug Name | Manufacturer | Indication |
|---|---|---|
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor dolutegravir | GSK | HIV infection AIDs |
| S/GSK1265744 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |

-continued

| Drug Name | Manufacturer | Indication |
|---|---|---|
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and Inhibitors of the entry of HIV into host cells. Meanwell, Nicholas A.; Kadow, John F., Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and U.S. Pat. No. 7,745,625.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

General Chemistry (Methods of Synthesis)

The present invention comprises compounds of Formulas I, II and III, their pharmaceutical formulations, and their use in patients suffering from or susceptible to HIV infection. The compounds of Formulas I, II and III also include pharmaceutically acceptable salts thereof. Procedures to construct compounds of Formulas I, II and III and intermediates useful for their synthesis are described after the Abbreviations.

Abbreviations

One or more of the following abbreviations, most of which are conventional abbreviations well known to those skilled in the art, may be used throughout the description of the disclosure and the examples:
RT=room temperature
BHT=2,6-di-tert-butyl-4-hydroxytoluene
CSA=camphorsulfonic acid
LDA=lithium diisopropylamide
KHMDS=potassium bis(trimethylsilyl)amide
SFC=supercritical fluid chromatography
Quant=quantitative
TBDMS=tert-butyldimethylsilane
PTFE=polytetrafluoroethylene
NMO=4-methylmorpholine-N-oxide
THF=tetrahydrofuran
TLC=thin layer chromatography
DCM=dichloromethane
DCE=dichloroethane
TFA=trifluoroacetic acid
LCMS=liquid chromatography mass spectroscopy
Prep=preparative
HPLC=high performance liquid chromatography
DAST=(diethylamino)sulfur trifluoride
TEA=triethylamine
DIPEA=N,N-diisopropylethylamine
HATU=[O-(7-azabenzotriazol-1-yl)-1,1,3,3-tetramethyluronium hexafluorophosphate]
DCC=N,N'-dicyclohexylcarbodiimide
DMAP=dimethylaminopyridine
TMS=trimethylsilyl
NMR=nuclear magnetic resonance
DPPA=diphenyl phosphoryl azide
AIBN=azobisisobutyronitrile
TBAF=tetrabutylammonium fluoride
DMF=dimethylformamide
TBTU=O-(benzotriazol-1-yl)-N,N,N',N'-tetramethyluronium tetrafluoroborate
Min(s)=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
µg=microgram(s)
µl=microliter(s)
µm=micrometer(s)
mm=millimeter(s)
Rpm=revolutions per minute
SM=starting material
TLC=thin layer chromatography
AP=area percentage
Equiv.=equivalent(s)
DMP=Dess-Martin periodinane
TMSCl=trimethylsilyl chloride
TBSCl=tert-Butyldimethylsilyl chloride
TBSOTf=trimethylsilyl trifluoromethanesulfonate
PhMe=toluene
PhNTf$_2$=N-Phenyl-bis(trifluoromethanesulfonimide)
S-Phos=2-Dicyclohexylphosphino-2',6'-dimethoxybiphenyl
TFDO=methyl(trifluoromethyl)dioxirane
TEMPO=2,2,6,6-tetramethylpiperidinyloxy
DI=deionized water The terms "C-3" and "C-28" refer to certain positions of a triterpene core as numbered in accordance with IUPAC rules (positions depicted below with respect to an illustrative triterpene: betulin):

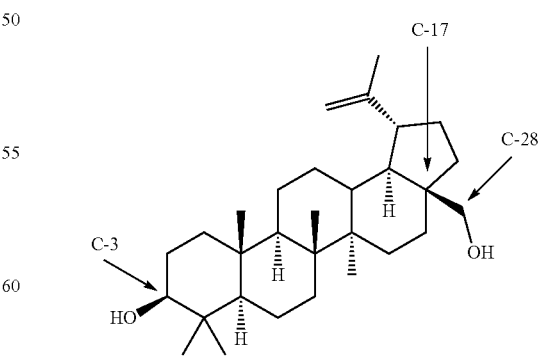

The same numbering is maintained when referring to the compound series in schemes and general descriptions of methods.

C-17

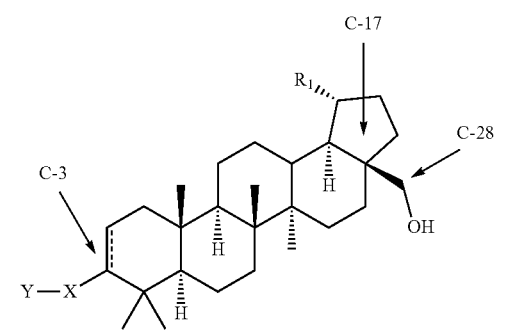

C-17 ureas

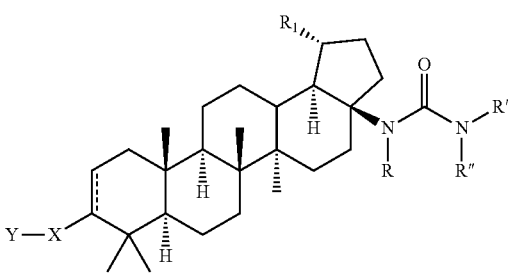

C-17 amides

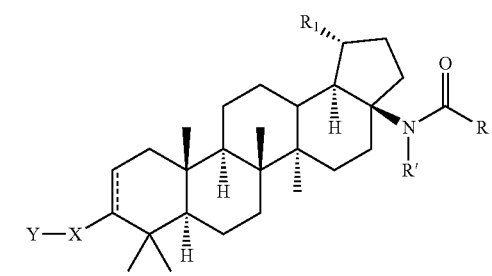

C-17 amines

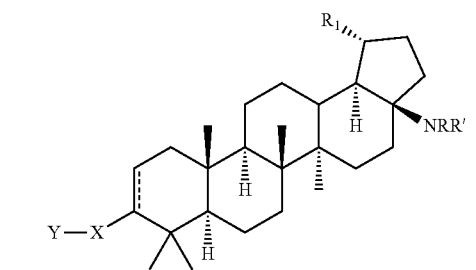

C-17 carbamates

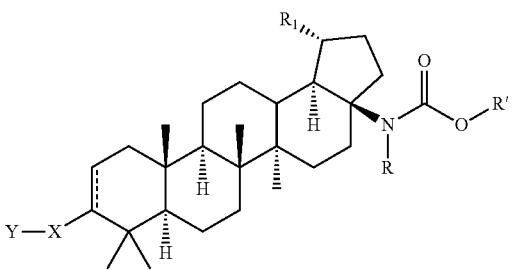

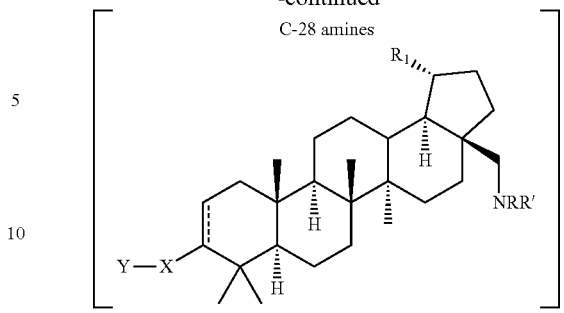

EXAMPLES

The following examples illustrate typical syntheses of the compounds of Formulas I, II and III as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B, or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), acetic-d4 (Acetic Acid d$_4$) ($\delta_H$ 11.6, 2.07), DMSO mix or DMSO-D6-CDCl$_3$ ($\delta_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods

Method 1
Start % B=0, Final % B=100 over 2 minute gradient, hold at 100% B
Flow Rate=1 mL/min
Wavelength=220 nm
Solvent A=90% water, 10% acetonitrile, 0.1% TFA
Solvent B=10% water, 90% acetonitrile, 0.1% TFA
Column=Phenomenex Luna C18, 3 μm, 2.0×30 mm Method 2
Start % B=0, Final % B=100 over 2 minute gradient, hold at 100% B
Flow Rate=1 mL/Min
Wavelength=220 nm
Solvent A=95% Water, 5% methanol/10 Mm ammonium acetate
Solvent B=5% Water, 95% methanol/10 Mm ammonium acetate
Column=Phenomenex Luna C18, 3 μm, 2.0×30 mm Method 3
Start % B=10, Final % B=100 over 18 minute gradient
Flow Rate=1 mL/Min
Wavelength=210 nm
Solvent A=5% acetonitrile, 95% water/0.01 M ammonium acetate
Solvent B=95% acetonitrile, 5% water/0.01 M ammonium acetate
Column=Waters Xbridge C8 2.5 µm, 4.6×50 mm
Method 4
Start % B=40, Final % B=100 over 18 minute gradient
Flow Rate=1 mL/Min
Wavelength=210 nm
Solvent A=20% acetonitrile, 80% water/0.05% TFA
Solvent B=80% acetonitrile, 20% water/0.05% TFA
Column=Sunfire C8, 5 µm, 4.6×50 mm
Prep HPLC Methods
Method 1
Start % B=20 Final % B=100 over 12 minute gradient, hold at 100% B
Flow Rate=40 mL/min
Solvent A=10% ACN-90% H$_2$O-0.1% TFA
Solvent B=90% ACN-10% H$_2$O-0.1% TFA
Column=Waters Sunfire 30×100 mm 5 µm
Method 2
Start % B=15 Final % B=100 over 12 minute gradient, hold at 100% B
Flow Rate=40 mL/min
Solvent A=10% ACN-90% H$_2$O-0.1% TFA
Solvent B=90% ACN-10% H$_2$O-0.1% TFA
Column=Waters Sunfire 30×100 mm 5 µm
Method 3
Start % B=25 Final % B=100 over 12 minute gradient, hold at 100% B
Flow Rate=40 mL/min
Solvent A=10% ACN-90% H$_2$O-0.1% TFA
Solvent B=90% ACN-10% H$_2$O-0.1% TFA
Column=Waters Sunfire 30×100 mm 5 µm
Method 4
Start % B=20 Final % B=90 over 30 minute gradient, hold at 100% B
Flow Rate=40 mL/min
Solvent A=10% ACN-90% H$_2$O-0.1% TFA
Solvent B=90% ACN-10% H$_2$O-0.1% TFA
Column=Waters Sunfire 30×100 mm 5 µm
Analytical HPLC Methods
Method 5
Start % B=40, Final % B=100 over 18 minute gradient
Flow Rate=1 mL/Min
Wavelength=210 nm
Solvent A=20% acetonitrile, 80% water/0.05% TFA
Solvent B=80% acetonitrile, 20% water/0.05% TFA
Column=Sunfire C8, 5 µm, 4.6×50 mm
Method 6
Start % B=40, Final % B=100 over 18 minute gradient
Flow Rate=1 mL/Min
Wavelength=210 nm
Solvent A=20% MeOH, 80% water/0.05% TFA
Solvent B=80% acetonitrile, 20% MeOH/0.05% TFA
Column=XTerra RP18, 3.5 µm, 4.6×50 mm Example 1

Preparation of (1R,3aS,4aS,4a1R,7aS,7a1R,8aR,12aS,12bR,14aR,14bR)-10-(4-carboxyphenyl)-4a1,6,6,7a1,9,9,12a-heptamethyl-1-(prop-1-en-2-yl)-2,3,3a,4,4a,4a1,7a,7a1,8,8a,9,12,12a,12b,13,14,14a,14b-octadecahydro-1H-cyclopenta[1,2]chryseno[4,5-def][1,3]dioxepine-3a-carboxylic acid

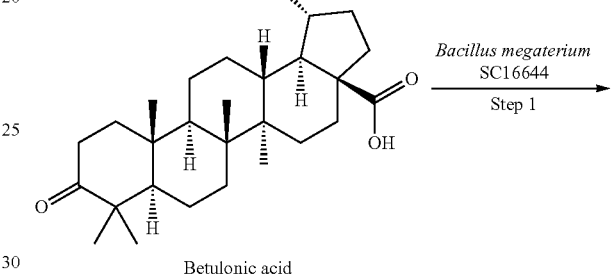

Betulonic acid

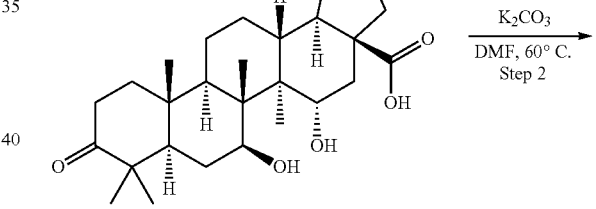

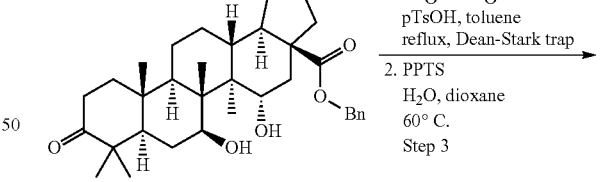

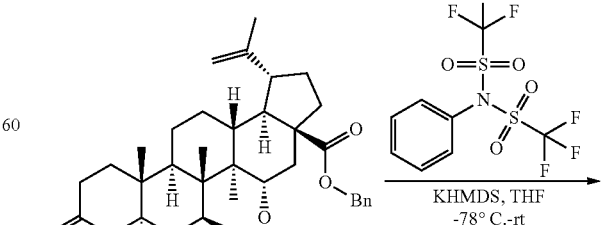

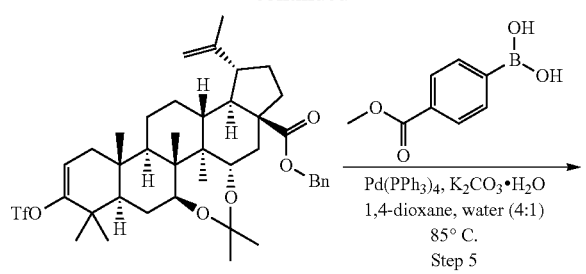

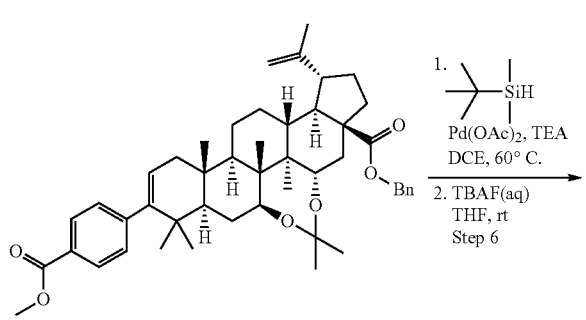

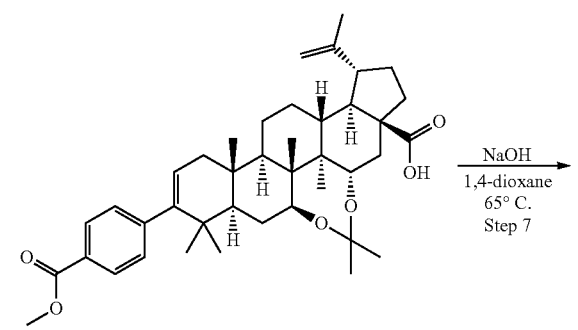

Example 1

Step 1: Preparation of (1R,3aS,5S,5aR,5bR,6S,7aR,11aR,13aR)-5,6-dihydroxy-5a,5b,8,8,11a-pentamethyl-9-oxo-1-(prop-1-en-2-yl)icosahydro-1H-cyclopenta[a]chrysene-3a-carboxylic acid (7β, 15α-dihydroxybetulonic acid)

Ingredients for SG-M2 medium are: Glucose monohydrate 22 g, Toasted Nutrisoy 5 g, Tastone154 5 g, $K_2HPO_4$ 5 g, deionized water 1000 mL. After mixing, the pH was adjusted to 7.0, and then autoclaved. One culture vial (1 mL) of *Bacillus megaterium* (SC16644, ATCC14581) was used to inoculate a 500 mL flask containing 100 mL of sterile SG-M2 medium. The flask was shaken at 30° C. and 250 rpm. After 29 h of growth, the stage 1 culture was used to inoculate (0.4% inoculation) sixteen 4 L flasks each with 500 mL of SG-M2 medium. The flasks were shaken at 30° C. and 250 rpm for 17 h. To each 4 L flask containing 500 mL stage 2 culture of *Bacillus megaterium* (SC16644, ATCC14581) was added a solution of betulonic acid (50 mg) in 5 mL of DMSO. A total of 800 mg betulonic acid (prepared as described in WO2013169578) was added to sixteen flasks. Biotransformation was conducted by shaking the 4 L flasks at 30° C. and 250 rpm. Biotransformation was monitored by taking out samples each day and analyzing by HPLC (Method 6) and LCMS (Method 3).

After four days, a dihydroxy product (MW 486, M+32) was found to be the major product peak with 5 to 15% of unreacted betulinic acid in different flasks. Biotransformation mixtures from all flasks were combined and acidified to pH 4.0 with 6 N HCl. Another 800 mL aqueous 0.01 M HCl was used to rinse all empty flasks and combined with the biotransformation mixture.

The mixture was filtered through a pad (200 g) of celite. The filtrate was extracted with 2 L of EtOAc. The EtOAc phase contained no dihydroxy product or betulonic acid, but contained a small amount (estimated to be about 28 mg by HPLC) of a possible trihydroxy product (MW 502). This 2 L EtOAc extract was used below. The soft cake together with the celite was transferred into a 3-L beaker and stirred vigorously with 1.6 L MeOH with an overhead stirrer for 1 h. The MeOH extract was collected by filtration.

The cake was again extracted with 1 L MeOH in the same way. Finally, the cake was treated in the filter funnel with 200 mL MeOH. All MeOH extracts were combined (2.8 L). The MeOH extract was concentrated on a rotary evaporator at 30° C. to about 200 mL, mixed with 200 mL of brine, and extracted twice (1.2 L and 0.8 L) with the above EtOAc extract containing the trihydroxy compound. The combined EtOAc extract was washed twice with 500 mL of brine and filtered through a filter paper. Removal of solvent from the EtOAc solution gave a brown residue, which was further dried in a vacuum oven at room temperature overnight to give 4.2 g of brown solid. The 4.2 g of brown solid was heated with a mixture of MeOH (10 mL) and EtOAc (10 mL) at 40° C. to give a brown solution. The solution was concentrated on a rotary evaporator to about 10 mL and immediately subjected to chromatography on a silica gel column packed with heptanes. The column was eluted with a mixture of heptanes-EtOAc-HOAc in a ratio of 90:10:0.5. When the front yellow color band came out, collection of small fractions (10 mL each) was started. The unreacted betulonic acid was eluted first in the fractions 5-10. The ratio of heptanes-EtOAc-HOAc was changed to 80:20:0.5 and then to 50:50:0.5. The fractions were collected and combined as five components (Table 1, Components 01, 02, 03, 04 and 05). After the completion of chromatography, the silica gel was poured into a beaker and stirred with 300 mL MeOH for 1 h and the MeOH solution was separated (Component 05A). Table 1 contains details of the separation of biotransformation mixture.

in an ice-bath for 1 h and then filtered providing 280 mg solid, MW 486, AP 50 (Table 1 Component 06).

The 280 mg solid, MW 486, AP 50 (Component 06) was dissolved in 100 mL EtOAc at 40° C. Heptane (100 mL) was added. The mixture was concentrated to about 20 mL. More heptane (100 mL) was added. The mixture was kept at room temperature for 1 h, and then in an ice-bath for 1 h, and filtered. The cake was dried in a vacuum oven at 30° C. overnight to give 146 mg off-white solid, HPLC retention time 9.9 min AP 87 (Component 08). LCMS and NMR indicated a dihydroxy-betulonic acid structure.

The filtrate was kept at room temperature overnight. The precipitate formed was filtered and gave 90 mg solid as the second crop, retention time 9.9 min product AP 35, a major impurity AP 62 (retention time 3.9 min, with strong UV 256 nm) (Table 1 Component 09). The second crop (Component 09) was subjected to silica gel (38 g) column chromatography and eluted with $CH_2Cl_2$ containing 5% MeOH and 3%

TABLE 1

Separation of *Bacillus megaterium* SC 16644 biotransformation mixture of betulonic acid

| Components | Descriptions | TLC with 50:50:1 of Heptane:EtOAc:HOAc | Weight | HPLC and LCMS MW (Molecular weight) AP (Area percent) |
|---|---|---|---|---|
|  | Crude mixture before chromatography | SM Rf 0.55 not collected; One major product spot Rf 0.15; Some minor spots. | 4.2 g |  |
| 01 | Fraction 17-23 | Rf 0.35 |  | No betulonic acid related compound peak |
| 02 | Fraction 29-35 | Rf 0.3 | 94 mg | MW 470, AP 23 |
| 03 | Fraction 41-45 | Rf 0.2 |  | No betulonic acid related compound peak |
| 04 | Fraction 59-68 | Major product Rf 0.15 | 0.5 g | MW 486, AP 38 |
| 05 | Fraction 78-108 | Rf 0.1 | 308 mg | MW 502, AP 19 |
| 05A | MeOH extract | Mixture Rf 0 to 0.1 |  | No betulonic acid related compound peak |
| 06 | Solid from 04 in MeOH-water |  | 280 mg | MW 486, AP 50 |
| 07 | Mother liquor of MeOH-water |  | 112 mg | Product AP 0.2 |
| 08 | First solid from 06 in EtOAc-heptane |  | 146 mg | Product AP 87 (9.9 min), 3.9 min impurity AP 8 |
| 09 | Second solid after 08 |  | 90 mg | Product AP 35, 3.9 min AP 62 |
| 10 | Mother liquor of EtOAc-heptane |  | 34 mg | Product AP 26, 3.9 min AP 36 |
| 11 | Chromatography of component 09, Fractions 22-25 |  | 72 mg | Product AP 85 (9.9 min) |

The different components (01, 02, 03, 04, 05) and MeOH solution (05A) were analyzed by TLC, HPLC (method 6) and LCMS (method 3). The components 01, 03 and 05A contained no peaks related to betulonic acid and were discarded. Components 02 (Solid 94 mg, MW 470, AP 23) and 05 (Solid 308 mg, MW 502, AP 19) were kept for separation and isolation of biotransformation products.

Component 04 (Major product, MW 486, AP 38, 0.5 g solid) was dissolved in MeOH at 40° C. The solution was concentrated to about 10 mL. Water (90 mL) was added slowly when a precipitate was formed. The mixture was kept HOAc. Fractions 22-25 (Table 1, Component 11) gave the product (retention time 9.9 min in HPLC), 72 mg, AP 85.

The first crop (146 mg, AP 87, Component 08) and chromatographically purified fraction from the second crop (72 mg, AP 85, Component 11) were combined and subjected to silica gel (42 g) column chromatography and eluted with $CH_2Cl_2$ containing 3% of MeOH and 3% of HOAc. Removal of solvent from the fractions 13-19 gave the title compound as a white solid (153 mg). HPLC AP 99.7 (method 6) LCMS: m/e 485.51 (M–H)$^-$, 10.29 min (method 3). Relevant $^1$H NMR signals: $^1$H NMR (500 MHz, MeOHd4) δ 4.71 (s, 1H), 4.62 (s, 1H), 3.95 (m, 1H), 3.78 (m, 1H), 3.00 (m, 1H), 2.4-2.6 (m, 3H), 2.14 (m, 1H), 2.04 (m, 1H), 1.85-1.95 (m, 2H), 1.74 (m, 1H), 1.70 (s, 3H).

Step 2: Preparation of (1R,3aS,5S,5aR,5bR,6S,7aR, 11aR,11bR,13aR,13bR)-benzyl 5,6-dihydroxy-5a, 5b,8,8,11a-pentamethyl-9-oxo-1-(prop-1-en-2-yl) icosahydro-1H-cyclopenta[a]chrysene-3a-carboxylate To a flask containing (1R,3aS,5S,5aR,5bR,6S,7aR,11aR, 11bR,13aR,13bR)-5,6-dihydroxy-5a,5b,8,8,11a-pentamethyl-9-oxo-1-(prop-1-en-2-yl)icosahydro-1H-cyclopenta [a]chrysene-3a-carboxylic acid (0.293 g, 0.602 mmol) was added potassium carbonate (0.250 g, 1.806 mmol). The mixture was diluted with DMF (5 mL) and benzyl bromide (0.079 mL, 0.662 mmol) was added. The mixture was heated to 60° C. for 16 h, then cooled to rt. The mixture was diluted with water (25 mL) and extracted with ethyl acetate (3×25 mL). The combined organic layers were washed with sat. aq. NaCl and dried over magnesium sulfate, filtered, and concentrated under reduced pressure. The residue was purified by flash chromatography using a 10-60% EtOAc in hexanes gradient with a 25 g silica gel column. The fractions containing the product were combined and concentrated under reduced pressure to give the title compound (0.306 g, 84% yield) as a white foam. $^1$H NMR (500 MHz, Chloroform-d) δ 7.44-7.30 (m, 5H), 5.20-5.10 (m, 2H), 4.72 (d, J=1.1 Hz, 1H), 4.63 (s, 1H), 3.79 (dd, J=11.2, 4.9 Hz, 1H), 2.98 (td, J=10.9, 4.7 Hz, 1H), 2.55 (dd, J=12.6, 4.7 Hz, 1H), 2.53-2.46 (m, 1H), 2.42-2.34 (m, 1H), 2.05-1.85 (m, 4H), 1.69 (s, 3H), 1.08 (s, 3H), 1.03 (s, 3H), 0.99 (s, 3H), 0.90 (s, 3H), 1.77-0.88 (m, 13H), 0.78 (s, 3H).

Step 3: Preparation of (1R,3aS,4aS,4a1R,7aS,7a1R, 8aR,12aR,12bR,14aR,14bR)-benzyl 4a1,6,6,7a1,9,9, 12a-heptamethyl-10-oxo-1-(prop-1-en-2-yl)icosahydro-1H-cyclopenta[1,2]chryseno[4,5-def][1,3] dioxepine-3a-carboxylate To a flask containing a solution of (1R,3aS,5S,5aR,5bR, 6S,7aR,11aR,11bR,13aR,13bR)-benzyl 5,6-dihydroxy-5a, 5b,8,8,11a-pentamethyl-9-oxo-1-(prop-1-en-2-yl)icosahydro-1H-cyclopenta[a]chrysene-3a-carboxylate (0.18 g, 0.312 mmol) in toluene (20 mL) was added 2,2-dimethoxypropane (0.384 mL, 3.12 mmol) and p-toluenesulfonic acid monohydrate (0.015 g, 0.078 mmol). The flask was attached to a Dean-Stark trap containing 4A molecular sieves in the side arm and the mixture was heated to reflux. After 1 h of heating, the mixture was cooled to rt and filtered through a plug of silica gel and celite which was then washed with DCM followed by a 25% EtOAc in hexanes solution. The filtrate was concentrated under reduced pressure. To the crude mixture of products in 1,4-dioxane (5 mL) was added water (0.2 mL) and pyridinium p-toluenesulfonate (0.020 g, 0.078 mmol). The mixture was warmed to 60° C. for 1 h then cooled to rt and filtered through a plug of silica gel and celite. The filtrate was concentrated under reduced pressure to give the title product (233 mg, quant.) as a yellow oil. $^1$H NMR (400 MHz, CHLOROFORM-d) δ 7.44-7.31 (m, 5H), 5.25 (d, J=12.0 Hz, 1H), 5.07 (d, J=12.0 Hz, 1H), 4.75 (d, J=2.0 Hz, 1H), 4.63 (s, 1H), 3.85 (dd, J=11.7, 5.1 Hz, 1H), 3.75-3.69 (m, 1H), 3.06-2.97 (m, 1H), 2.59-2.46 (m, 1H), 2.41-2.27 (m, 1H), 1.69 (s, 3H), 1.26 (s, 3H), 1.08 (s, 3H), 1.07 (s, 3H), 1.03 (s, 3H), 0.97 (s, 3H), 0.92 (s, 3H), 2.09-0.90 (m, 16H), 0.83 (s, 3H).

Step 4. Preparation of (1R,3aS,4aS,4a1R,7aS,7a1R, 8aR,12aR,12bR,14aR,14bR)-benzyl 4a1,6,6,7a1,9,9, 12a-heptamethyl-1-(prop-1-en-2-yl)-10-(((trifluoromethyl)sulfonyl)oxy)-2,3,3a,4,4a,4a1,7a,7a1,8,8a, 9,12,12a,12b,13,14,14a,14b-octadecahydro-1H-cyclopenta[1,2]chryseno[4,5-def][1,3]dioxepine-3a-carboxylate A solution of (1R,3aS,4aS,4a1R,7aS,7a1R,8aR,12aR, 12bR,14aR,14bR)-benzyl 4a1,6,6,7a1,9,9,12a-heptamethyl-10-oxo-1-(prop-1-en-2-yl)icosahydro-1H-cyclopenta[1,2] chryseno[4,5-def][1,3]dioxepine-3a-carboxylate (0.192 g, 0.312 mmol) and 1,1,1-trifluoro-N-phenyl-N-((trifluoromethyl)sulfonyl)methanesulfonamide (0.139 g, 0.390 mmol) was cooled to −78° C. To the solution was added KHMDS (0.91M in THF) (0.514 mL, 0.468 mmol) and the mixture was stirred at −78° C. for 1 h. The mixture was removed from the ice bath and was stirred at rt for 1.5 h. The mixture was diluted with water (15 mL) and extracted with ethyl acetate (3×20 mL). The combined organic layers were washed with brine, dried over magnesium sulfate, filtered and concentrated under reduced pressure. The residue was adsorbed to silica gel and purified by flash chromatography using a 0-15% EtOAc in hexanes gradient and a 25 g silica gel column. The fractions containing the product were combined and concentrated under reduced pressure to give the title product (0.18 g, 73.2% yield) as a yellow film. $^1$H NMR (500 MHz, CHLOROFORM-d) δ=7.42-7.31 (m, 5H), 5.57 (dd, J=6.6, 1.9 Hz, 1H), 5.24 (d, J=12.1 Hz, 1H), 5.07 (d, J=12.0 Hz, 1H), 4.75 (d, J=1.7 Hz, 1H), 4.63 (dd, J=2.0, 1.4 Hz, 1H), 3.84 (dd, J=11.7, 5.1 Hz, 1H), 3.72 (dd, J=11.4, 5.0 Hz, 1H), 3.01 (td, J=11.0, 4.6 Hz, 1H), 2.34 (dd, J=12.8, 5.0 Hz, 1H), 2.14-1.79 (m, 5H), 1.69 (s, 3H), 1.26 (s, 3H), 1.13 (s, 3H), 1.07 (s, 3H), 1.02 (s, 3H), 0.96 (s, 3H), 0.86 (s, 3H), 0.81 (s, 3H), 1.77-0.77 (m, 12H).

Step 5. Preparation of (1R,3aS,4aS,4a1R,7aS,7a1R, 8aR,12aS,12bR,14aR,14bR)-benzyl 10-(4-(methoxycarbonyl)phenyl)-4a1,6,6,7a1,9,9,12a-heptamethyl-1-(prop-1-en-2-yl)-2,3,3a,4,4a,4a1,7a,7a1, 8,8a,9,12,12a,12b,13,14,14a,14b-octadecahydro-1H-cyclopenta[1,2]chryseno[4,5-def][1,3]dioxepine-3a-carboxylate To a flask containing (1R,3aS,4aS,4a1R,7aS,7a1R,8aR, 12aR,12bR,14aR,14bR)-benzyl 4a1,6,6,7a1,9,9,12a-heptamethyl-1-(prop-1-en-2-yl)-10-(((trifluoromethyl)sulfonyl) oxy)-2,3,3a,4,4a,4a1,7a,7a1,8,8a,9,12,12a,12b,13,14,14a, 14b-octadecahydro-1H-cyclopenta[1,2]chryseno[4,5-def] [1,3]dioxepine-3a-carboxylate (0.18 g, 0.240 mmol) was added sodium carbonate hydrate (0.089 g, 0.721 mmol), 4-methoxycarbonylphenylboronic acid (0.052 g, 0.288 mmol) and palladium tetrakis (8.33 mg, 7.21 µmol). The mixture was diluted with 1,4-dioxane (2 mL) and water (0.5 mL), flushed with nitrogen and then heated to 85° C. After 3 h of heating, the mixture was cooled to rt, diluted with water (20 mL), and extracted with ethyl acetate (3×20 mL). The combined organic layers were washed with brine, dried over magnesium sulfate, filtered and concentrated under reduced pressure. The residue was adsorbed to silica gel and purified by flash chromatography using a 0-15% EtOAc in hexanes gradient and a 25 g silica gel column to give the title product (0.134 g, 72.1% yield) as a yellow foam. $^1$H NMR (400 MHz, CHLOROFORM-d) δ=7.93 (d, J=8.3 Hz, 2H), 7.44-7.30 (m, 5H), 7.19 (d, J=8.3 Hz, 2H), 5.29 (dd, J=6.0, 1.5 Hz, 1H), 5.25 (d, J=12.0 Hz, 1H), 5.08 (d, J=12.0 Hz, 1H), 4.76 (d, J=2.0 Hz, 1H), 4.65-4.62 (m, 1H), 3.92 (s, 3H), 3.87 (dd, J=11.8, 5.0 Hz, 1H), 3.77 (dd, J=11.3, 5.0 Hz, 1H), 3.03 (td, J=10.9, 4.3 Hz, 1H), 2.35 (dd, J=12.7, 5.1 Hz, 1H), 2.12-1.83 (m, 5H), 1.70 (s, 3H), 1.28 (s, 3H), 1.09 (s, 3H), 1.00 (s, 3H), 0.93 (s, 6H), 0.92 (br. s., 3H), 1.78-0.88 (m, 12H), 0.85 (s, 3H).

Step 6. Preparation of (1R,3aS,4aS,4a1R,7aS,7a1R, 8aR,12aS,12bR,14aR,14bR)-10-(4-(methoxycarbonyl)phenyl)-4a1,6,6,7a1,9,9,12a-heptamethyl-1-(prop-1-en-2-yl)-2,3,3a,4,4a,4a1,7a,7a1,8,8a,9,12,12a,12b,13,14,14a,14b-octadecahydro-1H-cyclopenta[1,2]chryseno[4,5-def][1,3]dioxepine-3a-carboxylic acid To a solution of (1R,3aS,4aS,4a1R,7aS,7a1R,8aR,12aS, 12bR,14aR,14bR)-benzyl 10-(4-(methoxycarbonyl)phenyl)-4a1,6,6,7a1,9,9,12a-heptamethyl-1-(prop-1-en-2-yl)-2,3,3a,4,4a,4a1,7a,7a1,8,8a,9,12,12a,12b,13,14,14a,14b-octadecahydro-1H-cyclopenta[1,2]chryseno[4,5-def][1,3]dioxepine-3a-carboxylate (0.127 g, 0.173 mmol) in DCE (2 mL) was added palladium(II) acetate (9.70 mg, 0.043 mmol), triethylamine (0.039 mL, 0.276 mmol) and t-butyldimethylsilane (0.057 mL, 0.346 mmol). The mixture was flushed with nitrogen then was heated to 60° C. After heating the mixture for 6 h, it was cooled to rt and was filtered through a pad of silica gel and celite. The filtrate was concentrated under reduced pressure and was used in the next step with no with no additional purification. $R_f$=0.45, 10% EtOAc in hexanes, stained with Hanessian's stain.

To the crude product above in THF (3 mL) was added TBAF (50% in $H_2O$) (0.090 g, 0.260 mmol). The mixture was stirred at rt for 30 minutes then was diluted with 1N HCl (5 mL) and water (3 mL) and then was extracted with ethyl acetate (3×15 mL). The organic layers were washed with brine, dried over magnesium sulfate, filtered, and concentrated under reduced pressure. The residue was adsorbed to silica gel and purified by flash chromatography using a 10-50% EtOAc in hexanes gradient and a 12 g silica gel column. The fractions containing the product were combined and concentrated under reduced pressure to give the title product (0.078 g, 69.9% yield) as an off-white solid. LCMS: m/e 643.35 (M-H)$^-$, 2.95 min (method 2). $^1$H NMR (400 MHz, CHLOROFORM-d) δ=7.94 (d, J=8.3 Hz, 2H), 7.20 (d, J=8.3 Hz, 2H), 5.33-5.28 (m, 1H), 4.79 (d, J=1.5 Hz, 1H), 4.66 (s, 1H), 4.17-4.10 (m, 1H), 3.92 (s, 3H), 3.83 (dd, J=11.3, 5.0 Hz, 1H), 3.01 (td, J=11.0, 4.6 Hz, 1H), 2.38 (dd, J=12.8, 5.0 Hz, 1H), 2.17-1.94 (m, 5H), 1.73 (s, 3H), 1.34 (s, 6H), 1.05 (s, 3H), 1.01 (s, 3H), 0.95 (br. s., 3H), 0.94 (s, 6H), 1.82-0.86 (m, 12H).

Step 7. To a solution of (1R,3aS,4aS,4a1R,7aS,7a1R,8aR, 12aS,12bR,14aR,14bR)-10-(4-(methoxycarbonyl)phenyl)-4a1,6,6,7a1,9,9,12a-heptamethyl-1-(prop-1-en-2-yl)-2,3,3a,4,4a,4a1,7a,7a1,8,8a,9,12,12a,12b,13,14,14a,14b-octadecahydro-1H-cyclopenta[1,2]chryseno[4,5-def][1,3]dioxepine-3a-carboxylic acid (28 mg, 0.043 mmol) in 1,4-dioxane (2 mL) was added 1N NaOH (0.217 mL, 0.217 mmol). The mixture was heated to 65° C. for 5 h, then was cooled to rt and diluted with 1N HCl (2 mL). The mixture was extracted with dichloromethane (3×7 mL) and the organic layers were dried over sodium sulfate. The drying agent was removed by filtration and the filtrate was concentrated under reduced pressure. The residue was purified by flash chromatography using a 0-7.5% MeOH in DCM gradient with 0.1% AcOH added to give the (1R,3aS,4aS,4a1R, 7aS,7a1R,8aR,12aS,12bR,14aR,14bR)-10-(4-carboxyphenyl)-4a1,6,6,7a1,9,9,12a-heptamethyl-1-(prop-1-en-2-yl)-2,3,3a,4,4a,4a1,7a,7a1,8,8a,9,12,12a,12b,13,14,14a,14b-octadecahydro-1H-cyclopenta[1,2]chryseno[4,5-def][1,3]dioxepine-3a-carboxylic acid (0.027 g, 100% yield) as a brown foam. LCMS: m/e 629.3 (M-H)$^-$, 2.54 min (method 2). $^1$H NMR (500 MHz, CHLOROFORM-d) δ=8.02 (d, J=8.0 Hz, 2H), 7.25 (d, J=8.2 Hz, 2H), 5.35-5.32 (m, 1H), 4.80 (s, 1H), 4.68 (s, 1H), 4.16 (dd, J=11.7, 5.0 Hz, 1H), 3.85 (dd, J=11.2, 5.0 Hz, 1H), 3.03 (td, J=11.1, 5.1 Hz, 1H), 2.40 (dd, J=12.8, 4.9 Hz, 1H), 2.18-1.96 (m, 4H), 1.74 (s, 3H), 1.36 (s, 6H), 1.82-1.19 (m, 13H), 1.06 (s, 3H), 1.03 (s, 3H), 0.99 (s, 3H), 0.97 (s, 6H).

Example 2

Preparation of (1R,3aS,5S,5aR,5bR,6S,7aR,11aS, 11bR,13aR,13bR)-9-(4-carboxyphenyl)-5,6-dihydroxy-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysene-3a-carboxylic acid

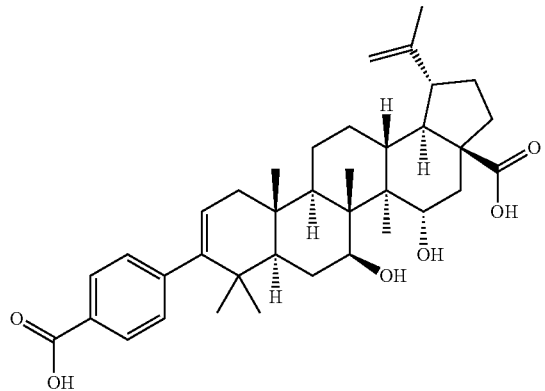

To a solution of (1R,3aS,4aS,4a1R,7aS,7a1R,8aR,12aS, 12bR,14aR,14bR)-10-(4-carboxyphenyl)-4a1,6,6,7a1,9,9, 12a-heptamethyl-1-(prop-1-en-2-yl)-2,3,3a,4,4a,4a1,7a,7a1, 8,8a,9,12,12a,12b,13,14,14a,14b-octadecahydro-1H-cyclopenta[1,2]chryseno[4,5-def][1,3]dioxepine-3a-carboxylic acid (0.02 g, 0.032 mmol) in THF (1 mL) was added HCl (1N) (0.5 mL, 0.500 mmol). The mixture was stirred at rt for 3 h, then was heated to 50° C. After heating the mixture for 15 h, it was cooled to rt. The mixture was diluted with 1 mL of 1,4-dioxane (solids had formed) and HCl (12M) (0.1 mL, 1.218 mmol) was added. The mixture was heated for 7.5 h then cooled to rt and concentrated. The residue was purified by prep HPLC (method 1). The fractions containing the product were combined and concentrated under reduced pressure to give the title compound (9.4 mg, 49.7% yield) as a white solid. LCMS: m/e 589.3 (M-H)$^-$, 2.40 min (method 2). $^1$H NMR (400 MHz, Acetic Acid-$d_4$) δ=8.00 (d, J=8.5 Hz, 2H), 7.26 (d, J=8.3 Hz, 2H), 5.33 (d, J=4.5 Hz, 1H), 4.76 (s, 1H), 4.64 (s, 1H), 4.06 (dd, J=11.3, 4.8 Hz, 1H), 3.92 (dd, J=11.0, 4.5 Hz, 1H), 3.01 (td, J=11.0, 4.4 Hz, 1H), 2.53 (dd, J=12.7, 4.6 Hz, 1H), 1.72 (s, 3H), 2.22-1.13 (m, 17H), 1.10 (s, 3H), 1.08 (s, 3H), 1.00 (s, 3H), 0.97 (s, 6H).

Example 3
Preparation of 4-((1R,3aS,5S,5aR,5bR,6S,7aR,11aS, 11bR,13aR,13bR)-3a-((2-(1,1-dioxidothiomorpholino)ethyl)amino)-5,6-dihydroxy-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
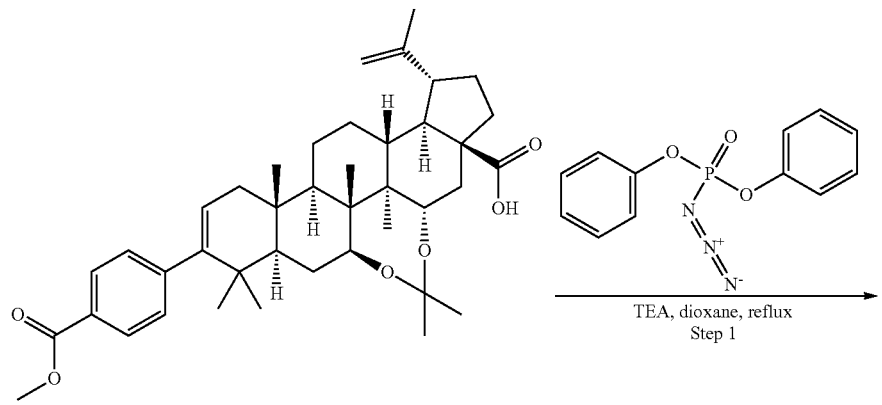
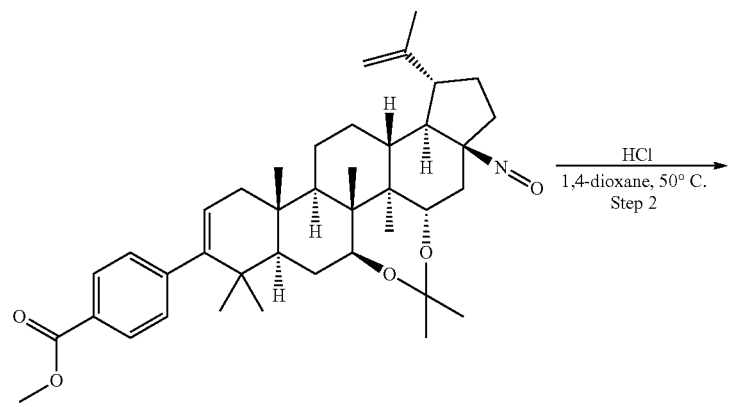
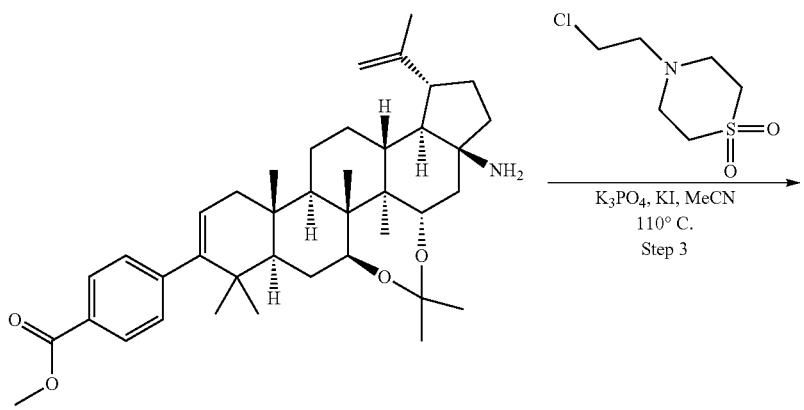

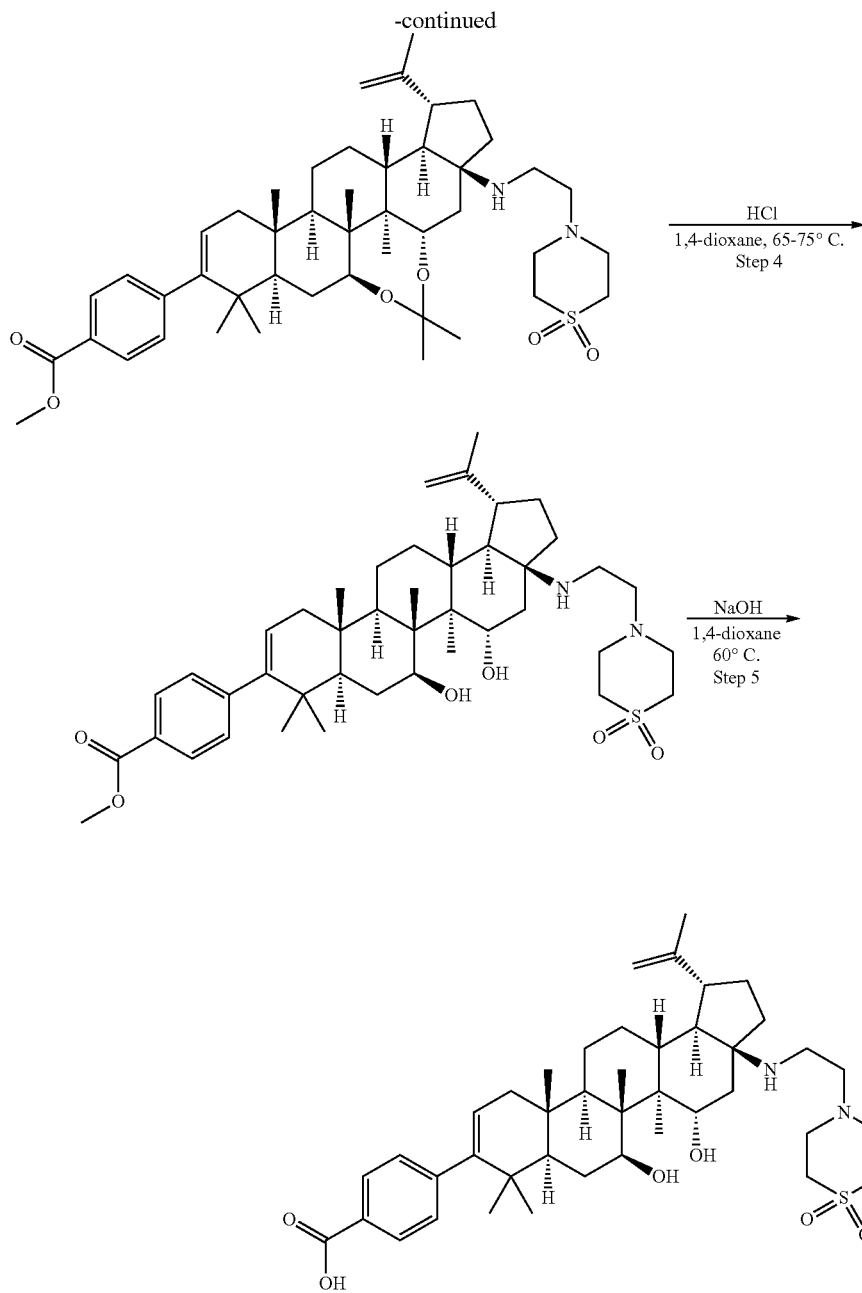

Example 3

Step 1. Preparation of methyl 4-((1R,3aS,4aS,4a1R, 7aS,7a1R,8aR,12aS,12bR,14aR,14bR)-3a-isocyanato-4a1,6,6,7a1,9,9,12a-heptamethyl-1-(prop-1-en-2-yl)-2,3,3a,4,4a,4a1,7a,7a1,8,8a,9,12,12a,12b,13,14,14a,14b-octadecahydro-1H-cyclopenta[1,2]chryseno[4,5-def][1,3]dioxepin-10-yl)benzoate To a solution of (1R,3aS,4aS,4a1R,7aS,7a1R,8aR,12aS, 12bR,14aR,14bR)-10-(4-(methoxycarbonyl)phenyl)-4a1,6, 6,7a1,9,9,12a-heptamethyl-1-(prop-1-en-2-yl)-2,3,3a,4,4a, 4a1,7a,7a1,8,8a,9,12,12a,12b,13,14,14a,14b-octadecahydro-1H-cyclopenta[1,2]chryseno[4,5-def][1,3] dioxepine-3a-carboxylic acid (0.045 g, 0.070 mmol) in 1,4-dioxane (5 mL) was added TEA (0.029 mL, 0.209 mmol) followed by diphenyl phosphorazidate (0.023 mL, 0.105 mmol). The mixture was heated to reflux for 19 h, then it was cooled to rt. The mixture was concentrated under reduced pressure, adsorbed to silica gel, and purified by flash chromatography using a 0-10% EtOAc in hexanes gradient and a 12 g silica gel column. The fractions containing the expected product were combined and concentrated under reduced pressure to give the title product (0.033 g, 0.051 mmol, 73.7% yield) as a clear, colorless film. $^1$H NMR (400 MHz, CHLOROFORM-d) δ=7.94 (d, J=8.3 Hz, 2H), 7.20 (d, J=8.3 Hz, 2H), 5.33-5.28 (m, 1H), 4.78 (d, J=1.3 Hz, 1H), 4.68 (s, 1H), 4.23 (dd, J=11.3, 5.3 Hz, 1H), 3.92 (s, 3H), 3.82 (dd, J=11.3, 5.0 Hz, 1H), 2.52 (td, J=10.9, 5.9 Hz, 1H), 2.20-2.00 (m, 3H), 1.71 (s, 3H), 1.35 (s, 3H), 1.34 (s, 3H), 1.11 (s, 3H), 1.00 (s, 3H), 0.97 (br. s., 3H), 0.96 (s, 6H), 1.97-0.79 (m, 15H).

Step 2. Preparation of methyl 4-((1R,3aS,4aS,4a1R, 7aS,7a1R,8aR,12aS,12bR,14aR,14bR)-3a-amino-4a1,6,6,7a1,9,9,12a-heptamethyl-1-(prop-1-en-2-yl)-2,3,3a,4,4a,4a1,7a,7a1,8,8a,9,12,12a,12b,13,14,14a, 14b-octadecahydro-1H-cyclopenta[1,2]chryseno[4,5-def][1,3]dioxepin-10-yl)benzoate To a solution of methyl 4-((1R,3aS,4aS,4a1R,7aS,7a1R, 8aR,12aS,12bR,14aR,14bR)-3a-isocyanato-4a1,6,6,7a1,9,9, 12a-heptamethyl-1-(prop-1-en-2-yl)-2,3,3a,4,4a,4a1,7a,7a1, 8,8a,9,12,12a,12b,13,14,14a,14b-octadecahydro-1H-cyclopenta[1,2]chryseno[4,5-def][1,3]dioxepin-10-yl) benzoate (0.03 g, 0.047 mmol) in 1,4-dioxane (2 mL) was added HCl (37%) (0.077 mL, 0.935 mmol). The mixture was warmed to 50° C. for 15 h, then cooled to rt and concentrated under reduced pressure. The residue was purified by flash chromatography using a 0-7% MeOH in DCM gradient and a 12 g silica gel column. The fractions containing the product were combined and concentrated under reduced pressure. The mixture was purified further by prep HPLC (method 2). The fractions containing the product were combined and concentrated under reduced pressure to give the title product (20 mg, 0.032 mmol, 69.5% yield) as an off-white solid. LCMS: m/e 616.6 (M+H)$^+$, 2.05 min (method 1). $^1$H NMR (400 MHz, CHLOROFORM-d) δ 7.94 (d, J=8.3 Hz, 2H), 7.19 (d, J=8.5 Hz, 2H), 5.33-5.28 (m, 1H), 4.83 (s, 1H), 4.72 (s, 1H), 4.16 (dd, J=11.8, 5.3 Hz, 1H), 3.92 (s, 3H), 3.83 (dd, J=11.3, 5.0 Hz, 1H), 2.72-2.60 (m, 1H), 2.35-2.17 (m, 2H), 1.73 (s, 3H), 1.12 (s, 3H), 1.04 (s, 3H), 2.14-0.87 (m, 31H).

Step 3. Preparation of methyl 4-((1R,3aS,4aS,4a1R, 7aS,7a1R,8aR,12aS,12bR,14aR,14bR)-3a-((2-(1,1-dioxidothiomorpholino)ethyl)amino)-4a1,6,6,7a1,9, 9,12a-heptamethyl-1-(prop-1-en-2-yl)-2,3,3a,4,4a, 4a1,7a,7a1,8,8a,9,12,12a,12b,13,14,14a,14b-octadecahydro-1H-cyclopenta[1,2]chryseno[4,5-def] [1,3]dioxepin-10-yl)benzoate To a sealable vial containing methyl 4-((1R,3aS,4aS, 4a1R,7aS,7a1R,8aR,12aS,12bR,14aR,14bR)-3a-amino-4a1, 6,6,7a1,9,9,12a-heptamethyl-1-(prop-1-en-2-yl)-2,3,3a,4, 4a,4a1,7a,7a1,8,8a,9,12,12a,12b,13,14,14a,14b-octadecahydro-1H-cyclopenta[1,2]chryseno[4,5-def][1,3] dioxepin-10-yl)benzoate (20 mg, 0.032 mmol) and 4-(2-chloroethyl)thiomorpholine 1,1-dioxide (19.26 mg, 0.097 mmol) was added potassium iodide (16.17 mg, 0.097 mmol) and phosphoric acid, potassium salt (34.5 mg, 0.162 mmol). The mixture was diluted with acetonitrile (1 mL), flushed with nitrogen, then sealed and heated to 110° C. for 15 h. The mixture was concentrated under reduced pressure and adsorbed to silica gel then was purified by flash chromatography using a 10-60% EtOAc in hexanes gradient and a 4 g silica gel column. The fractions containing the product were combined and concentrated under reduced pressure to give the title product (16 mg, 0.021 mmol, 63.4% yield) as a clear film. LCMS: m/e 777.7 (M+H)$^+$, 1.96 min (method 1). $^1$H NMR (500 MHz, CHLOROFORM-d) δ 7.94 (d, J=8.2 Hz, 2H), 7.20 (d, J=8.2 Hz, 2H), 5.31-5.28 (m, 1H), 4.74 (s, 1H), 4.64 (br. s., 1H), 4.16-4.10 (m, 1H), 3.91 (s, 3H), 3.81 (dd, J=11.2, 4.7 Hz, 1H), 3.15-3.00 (m, 9H), 2.72-2.65 (m, 2H), 2.64-2.55 (m, 2H), 2.46 (td, J=10.7, 5.4 Hz, 1H), 1.70 (s, 3H), 1.33 (s, 3H), 1.28 (s, 3H), 1.08 (s, 3H), 1.01 (s, 3H), 0.95 (s, 9H), 2.14-0.79 (m, 17H).

Step 4. Preparation of methyl 4-((1R,3aS,5S,5aR, 5bR,6S,7aR,11aS,11bR,13aR,13bR)-3a-((2-(1,1-dioxidothiomorpholino)ethyl)amino)-5,6-dihydroxy-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoate To a solution of methyl 4-((1R,3aS,4aS,4a1R,7aS,7a1R, 8aR,12aS,12bR,14aR,14bR)-3a-((2-(1,1-dioxidothiomorpholino)ethyl)amino)-4a1,6,6,7a1,9,9,12a-heptamethyl-1-(prop-1-en-2-yl)-2,3,3a,4,4a,4a1,7a,7a1,8,8a,9,12,12a,12b, 13,14,14a,14b-octadecahydro-1H-cyclopenta[1,2]chryseno [4,5-def][1,3]dioxepin-10-yl)benzoate (0.016 g, 0.021 mmol) in 1,4-dioxane (0.5 mL) was added 1N HCl (0.051 mL, 0.618 mmol). The mixture was heated to 75° C. for 8 h then cooled to 60° C. and stirred for an additional 14.5 h. The mixture was cooled to rt and purified by prep HPLC (method 3). The fractions containing the product were combined and concentrated under reduced pressure to give the title product (4.0 mg, 5.4 μmol, 26% yield) as a clear film. LCMS: m/e 737.6 (M+H)$^+$, 1.82 min (method 1).

Step 5. To a solution of methyl 4-((1R,3aS,5S,5aR,5bR, 6S,7aR,11aS,11bR,13aR,13bR)-3a-((2-(1,1-dioxidothiomorpholino)ethyl)amino)-5,6-dihydroxy-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (0.004 g, 5.43 μmol) in 1,4-dioxane (0.25 mL) was added NaOH (1N) (0.054 mL, 0.054 mmol). The mixture was heated to 60° C. for 14.5 h then was cooled to rt and purified by prep HPLC (method 1). The fractions containing the expected product were combined and concentrated under reduced pressure to give. Because the purity of the compound was not sufficient, it was purified a second time by prep HPLC (method 4). The fractions containing the product were combined and concentrated under reduced pressure to give the TFA salt of 4-((1R,3aS,5S,5aR,5bR,6S, 7aR,11aS,11bR,13aR,13bR)-3a-((2-(1,1-dioxidothiomorpholino)ethyl)amino)-5,6-dihydroxy-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid (1.1 mg, 1.3 μmol, 24% yield) as an off-white solid. LCMS: m/e 723.7 (M+H)$^+$, 1.51 min (method 1).

Example 4
Preparation of (1S,3aS,5aR,5bR,7aS,11aS,11bS,13aR,13bR)-9-(4-carboxyphenyl)-1-isopropyl-5a,5b,8,8,11a-pentamethyl-11-oxo-2,3,3a,4,5,5a,5b,6,7,7a,8,11,11a,11b,12,13,13a,13b-octadecahydro-1H-cyclopenta[a]chrysene-3a-carboxylic acid
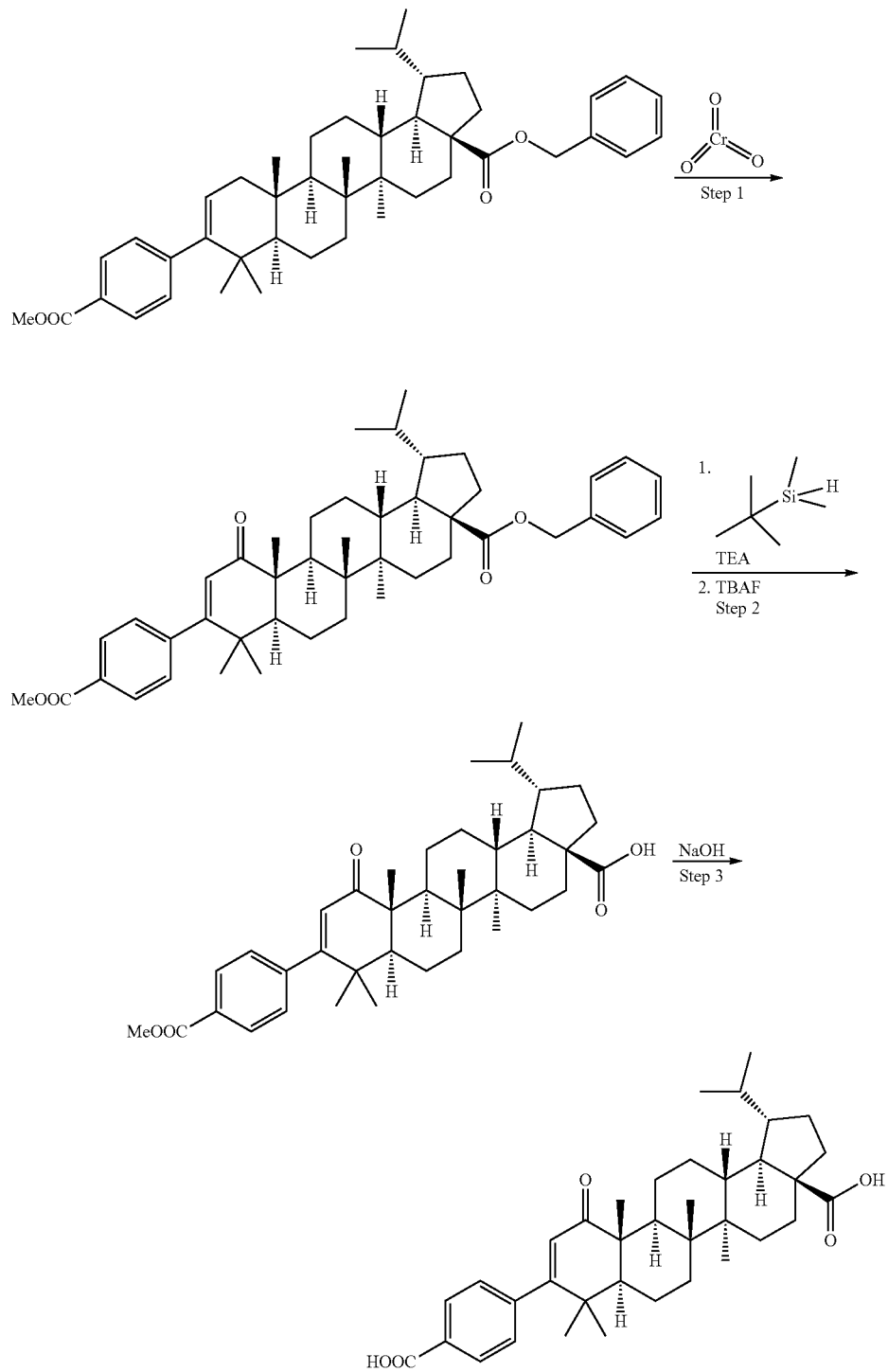
Example 4

Step 1. Preparation of (1S,3aS,5aR,5bR,7aS,11aS, 11bS,13aR,13bR)-benzyl 1-isopropyl-9-(4-(methoxycarbonyl)phenyl)-5a,5b,8,8,11a-pentamethyl-11-oxo-2,3,3a,4,5,5a,5b,6,7,7a,8,11,11a,11b, 12,13,13a,13b-octadecahydro-1H-cyclopenta[a]chrysene-3a-carboxylate To a mixture of chromium(VI) oxide (752 mg, 7.52 mmol) in DCM (10 mL) was added pyfidine (1.216 mL, 15.04 mmol), the reaction mixture was stirred for 2 hours at 20° C. Then (1S,3aS,5aR,5bR,7aR,11aS,11bR,13aR,13bR)-benzyl 1-isopropyl-9-(4-(methoxycarbonyl)phenyl)-5a,5b, 8,8,11a-pentamethyl-2,3,3a,4,5,5a,5b,6,7,7a,8,11,11a,11b, 12,13,13a,13b-octadecahydro-1H-cyclopenta[a]chrysene-3a-carboxylate (500 mg, 0.752 mmol) (prepared as described in WO201153319) was added and the reaction mixture was stirred for 30 h. The reaction was filtered and washed with 1 N HCl (10 mL) and sat. sodium bicarbonate (15 mL). The organic layer was dried over sodium sulfate, filtered and concentrated under reduced pressure. The residue was purified by flash chromatography with 0-15% ethyl acetate/hexanes to give the title product as a white solid. (210 mg, 41%). LCMS: m/e 679.3 (M+H)$^+$, 3.50 min (method 2).

Step 2. Preparation of (1S,3aS,5aR,5bR,7aS,11aS, 11bS,13aR,13bR)-1-isopropyl-9-(4-(methoxycarbonyl)phenyl)-5a,5b,8,8,11a-pentamethyl-11-oxo-2,3, 3a,4,5,5a,5b,6,7,7a,8,11,11a,11b,12,13,13a,13b-octadecahydro-1H-cyclopenta[a]chrysene-3a-carboxylic acid A mixture of (1S,3aS,5aR,5bR,7aS,11aS,11bS,13aR, 13bR)-benzyl 1-isopropyl-9-(4-(methoxycarbonyl)phenyl)-5a,5b,8,8,11a-pentamethyl-11-oxo-2,3,3a,4,5,5a,5b,6,7,7a, 8,11,11a,11b,12,13,13a,13b-octadecahydro-1H-cyclopenta [a]chrysene-3a-carboxylate (270 mg, 0.398 mmol), palladium acetate (17.86 mg, 0.080 mmol) tert-butyldimethylsilane (60.1 mg, 0.517 mmol) and TEA (0.166 mL, 1.193 mmol) in dichloroethane (5 mL) was heated up at 60° C. for 3 h. The reaction mixture was filtered through a pad of celite, then concentrated under reduced pressure to provide the corresponding silyl ester intermediate. To this intermediate in tetrahydrofuran (5 mL) was added TBAF (693 mg, 1.988 mmol). The reaction mixture was stirred for 3 h at room temperature. The mixture was concentrated under reduced pressure and the residue was purified by flash chromatography with 0-40% ethyl acetate/hexanes to provide the title product as a white solid (150 mg, 64%). LCMS: m/e 589.6 (M+H)$^+$, 2.61 min (method 1).

Step 3. Preparation of (1S,3aS,5aR,5bR,7aS,11aS, 11bS,13aR,13bR)-9-(4-carboxyphenyl)-1-isopropyl-5a,5b,8,8,11a-pentamethyl-11-oxo-2,3,3a,4,5,5a,5b, 6,7,7a,8,11,11a,11b,12,13,13a,13b-octadecahydro-1H-cyclopenta[a]chrysene-3a-carboxylic acid A mixture of (1S,3aS,5aR,5bR,7aS,11aS,11bS,13aR, 13bR)-1-isopropyl-9-(4-(methoxycarbonyl)phenyl)-5a,5b, 8,8,11a-pentamethyl-11-oxo-2,3,3a,4,5,5a,5b,6,7,7a,8,11, 11a,11b,12,13,13a,13b-octadecahydro-1H-cyclopenta[a] chrysene-3a-carboxylic acid (8 mg, 0.014 mmol) and 1N sodium hydroxide (0.068 mL, 0.068 mmol) in dioxane (1 mL) was refluxed for 3 h. After cooling to room temperature, the reaction mixture was filtered and purified by HPLC to provide the desired product as a white solid (4.2 mg, 51%). LCMS: m/e 575.2 (M+H)$^+$, 2.39 min (method 2). $^1$H NMR (400 MHz, Acetic) δ 8.08 (d, J=8.3 Hz, 2H), 7.34 (d, J=8.3 Hz, 2H), 5.67 (s, 1H), 2.49-1.08 (m, 22H), 1.38 (s, 3H), 1.21 (s, 3H), 1.10 (s, 3H), 1.06 (s, 3H), 1.05 (s, 3H), 0.88 (d, J=7.0 Hz, 3H), 0.81 (d, J=6.8 Hz, 3H).

Example 5 and Example 6

Preparation of (1S,3aS,5aR,5bR,7aS,11S,11aS,11bS, 13aR,13bR)-9-(4-carboxyphenyl)-11-hydroxy-1-isopropyl-5a,5b,8,8,11a-pentamethyl-2,3,3a,4,5,5a, 5b,6,7,7a,8,11,11a,11b,12,13,13a,13b-octadecahydro-1H-cyclopenta[a]chrysene-3a-carboxylic acid and (1S,3aS,5aR,5bR,7aS,11R, 11aS,11bS,13aR,13bR)-9-(4-carboxyphenyl)-11-hydroxy-1-isopropyl-5a,5b,8,8,11a-pentamethyl-2,3, 3a,4,5,5a,5b,6,7,7a,8,11,11a,11b,12,13,13a,13b-octadecahydro-1H-cyclopenta[a]chrysene-3a-carboxylic acid

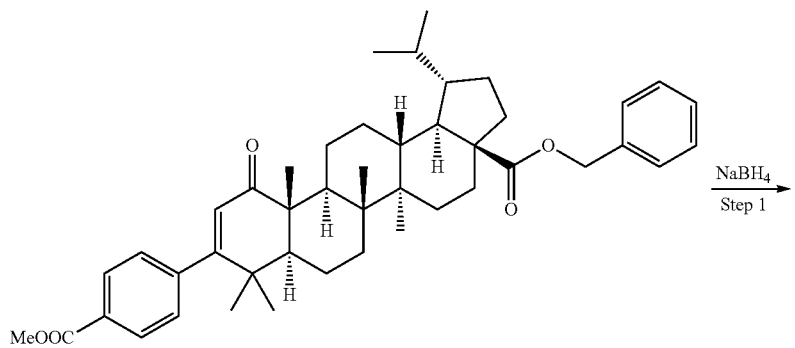

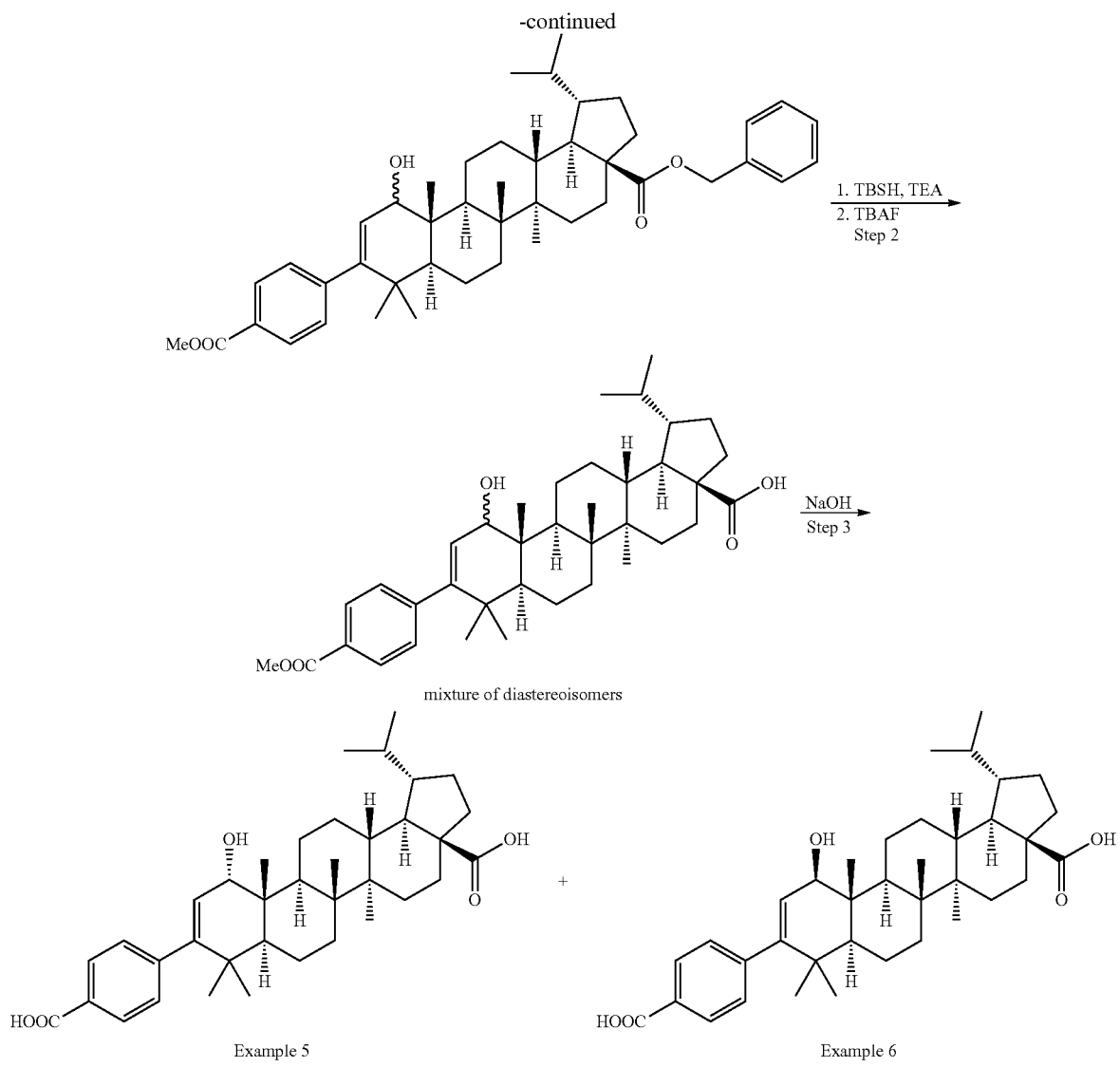

Example 5

Example 6

Step 1. Preparation of (1S,3aS,5aR,5bR,7aS,11aS,11bS,13aR,13bR)-benzyl 11-hydroxy-1-isopropyl-9-(4-(methoxycarbonyl)phenyl)-5a,5b,8,8,11a-pentamethyl-2,3,3a,4,5,5a,5b,6,7,7a,8,11,11a,11b,12,13,13a,13b-octadecahydro-1H-cyclopenta[a]chrysene-3a-carboxylate To a solution of (1S,3aS,5aR,5bR,7aS,11aS,11bS,13aR,13bR)-benzyl 1-isopropyl-9-(4-(methoxycarbonyl)phenyl)-5a,5b,8,8,11a-pentamethyl-11-oxo-2,3,3a,4,5,5a,5b,6,7,7a,8,11,11a,11b,12,13,13a,13b-octadecahydro-1H-cyclopenta[a]chrysene-3a-carboxylate (20 mg, 0.029 mmol) in methanol (1 mL) and dioxane (1 mL) was added sodium borohydride (22.29 mg, 0.589 mmol) at 0° C. The reaction mixture was stirred at 20° C. for 18 h. The reaction mixture was quenched with distilled water (3 mL) and extracted with ethyl acetate (3×4 mL). All the extracts were combined, dried over sodium sulfate, filtered and concentrated under reduced pressure. The residue was purified by flash chromatography with 0-20% ethyl acetate/hexanes to provide the desired product as a white solid (20 mg, 100%). LCMS: m/e 663.3 (M-18+H)$^+$, 3.26, 3.39 min (method 2).

Step 2. Preparation of (1S,3aS,5aR,5bR,7aS,11aS,11bS,13aR,13bR)-11-hydroxy-1-isopropyl-9-(4-(methoxycarbonyl)phenyl)-5a,5b,8,8,11a-pentamethyl-2,3,3a,4,5,5a,5b,6,7,7a,8,11,11a,11b,12,13,13a,13b-octadecahydro-1H-cyclopenta[a]chrysene-3a-carboxylic acid A mixture of (1S,3aS,5aR,5bR,7aS,11aS,11bS,13aR,13bR)-benzyl 11-hydroxy-1-isopropyl-9-(4-(methoxycarbonyl)phenyl)-5a,5b,8,8,11a-pentamethyl-2,3,3a,4,5,5a,5b,6,7,7a,8,11,11a,11b,12,13,13a,13b-octadecahydro-1H-cyclopenta[a]chrysene-3a-carboxylate (20 mg, 0.029 mmol), palladium acetate (1.32 mg, 0.006 mmol) tert-butyldimethylsilane (10.25 mg, 0.088 mmol) and TEA (0.012 mL, 0.088 mmol) in dichloroethane (1 mL) was heated up at 60° C. for 3 h. The reaction mixture was filtered through a pad of celite, then concentrated under reduced pressure to provide the silyl ester intermediate. To this intermediate in dioxane (1 mL) was added TBAF (0.117 mL, 0.117 mmol). The reaction mixture was stirred for 3 h at room temperature and then concentrated under reduced pressure. The residue was purified by flash chromatography with 0-45% ethyl acetate/hexanes to provide the mixture of two isomers (15 mg, 86%). LCMS: m/e 589.4 (M−H)⁻, 2.65, 2.76 min (method 2).

Step 3. A mixture of (1S,3aS,5aR,5bR,7aS,11aS,11bS, 13aR,13bR)-11-hydroxy-1-isopropyl-9-(4-(methoxycarbonyl)phenyl)-5a,5b,8,8,11a-pentamethyl-2,3,3a,4,5,5a,5b,6, 7,7a,8,11,11a,11b,12,13,13a,13b-octadecahydro-1H-cyclopenta[a]chrysene-3a-carboxylic acid (15 mg, 0.025 mmol) and 1N sodium hydroxide (0.124 mL, 0.124 mmol) in dioxane (1 mL) was heated up at 78° C. for 3 h. The reaction mixture was filtered and the clear solution was purified by HPLC to give the title compounds as white solids: Example 5: (1S,3aS,5aR,5bR,7aS,11S,11aS,11bS, 13aR,13bR)-9-(4-carboxyphenyl)-11-hydroxy-1-isopropyl-5a,5b,8,8,11a-pentamethyl-2,3,3a,4,5,5a,5b,6,7,7a,8,11,11a, 11b,12,13,13a,13b-octadecahydro-1H-cyclopenta[a]chrysene-3a-carboxylic acid (6 mg, 40%). LCMS: m/e 575.4 (M−H)⁻, 2.23 min (method 2). ¹H NMR (500 MHz, Acetic) δ 8.05 (d, J=8.2 Hz, 2H), 7.32 (d, J=8.2 Hz, 2H), 5.61 (d, J=5.8 Hz, 1H), 3.92 (d, J=6.1 Hz, 1H), 2.44-1.17 (m, 22H), 1.10 (s, 3H), 1.09 (s, 3H), 1.04 (s, 3H), 1.01 (s, 3H), 1.00 (s, 3H), 0.92 (d, J=6.7 Hz, 3H), 0.84 (d, J=6.7 Hz, 3H). and Example 6: (1S,3aS,5aR,5bR,7aS,11R,11aS,11bS,13aR, 13bR)-9-(4-carboxyphenyl)-11-hydroxy-1-isopropyl-5a,5b, 8,8,11a-pentamethyl-2,3,3a,4,5,5a,5b,6,7,7a,8,11,11a,11b, 12,13,13a,13b-octadecahydro-1H-cyclopenta[a]chrysene-3a-carboxylic acid (4 mg, 27%). LCMS: m/e 575.4 (M−H)⁻, 2.60 min (method 2). ¹H NMR (500 MHz, Acetic) δ 8.05 (d, J=8.2 Hz, 2H), 7.32 (d, J=8.5 Hz, 2H), 5.20 (d, J=1.5 Hz, 1H), 4.20 (d, J=1.5 Hz, 1H), 2.56-2.24 (m, 4H), 1.97-1.83 (m, 2H), 1.78-1.22 (m, 16H), 1.12 (s, 3H), 1.09 (s, 3H), 1.08 (s, 3H), 1.03 (s, 3H), 0.99 (s, 3H), 0.92 (d, J=7.0 Hz, 3H), 0.84 (d, J=6.7 Hz, 3H).

Example 7 and Example 8

Preparation of (1S,3aS,5aR,5bR,7aS,11S,11aS,11bS, 13aR,13bR)-9-(4-carboxyphenyl)-11-hydroxy-1-isopropyl-5a,5b,8,8,11a-pentamethyl-2,3,3a,4,5,5a, 5b,6,7,7a,8,11,11a,11b,12,13,13a,13b-octadecahydro-1H-cyclopenta[a]chrysene-3a-carboxylic acid and (1S,3aS,5aR,5bR,7aS,11R, 11aS,11bS,13aR,13bR)-9-(4-carboxyphenyl)-11-hydroxy-1-isopropyl-5a,5b,8,8,11a-pentamethyl-2,3, 3a,4,5,5a,5b,6,7,7a,8,11,11a,11b,12,13,13a,13b-octadecahydro-1H-cyclopenta[a]chrysene-3a-carboxylic acid

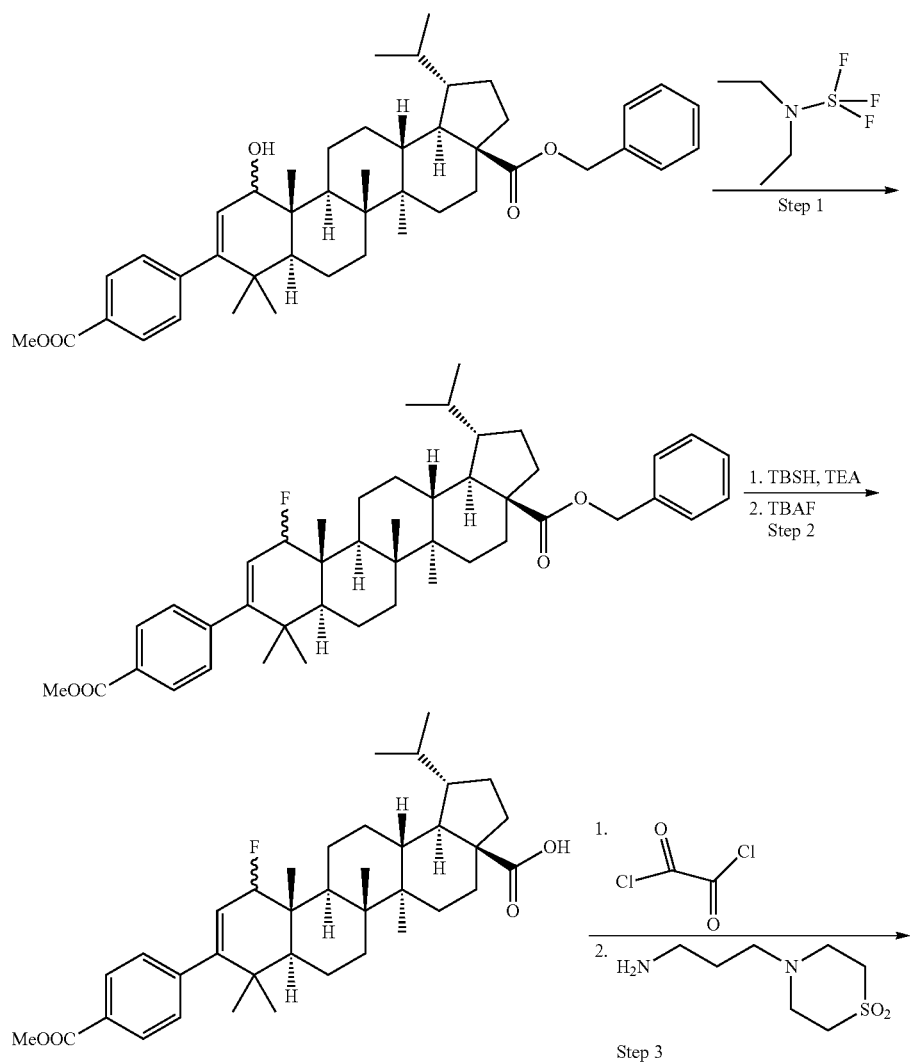

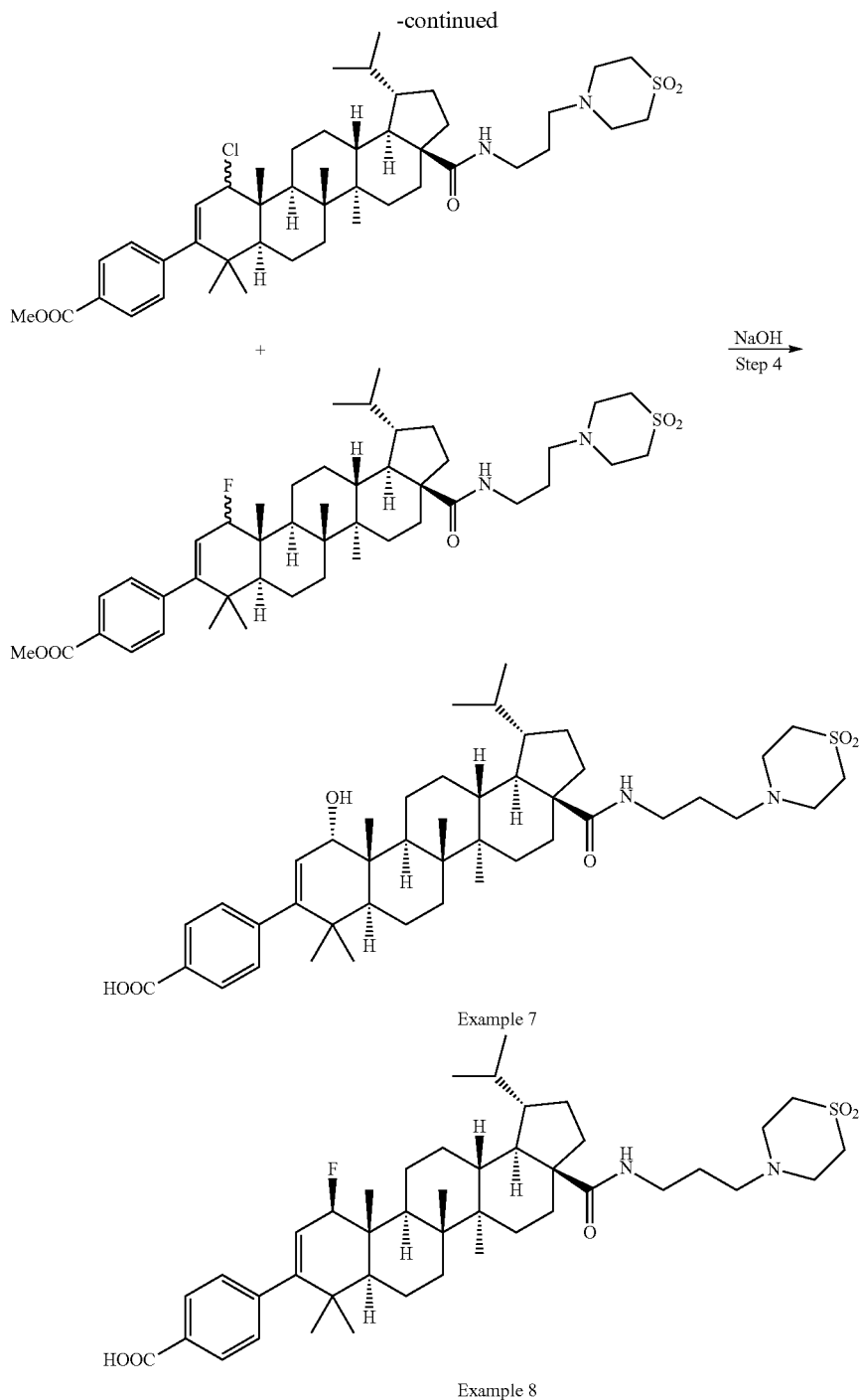

Example 7

Example 8

Step 1. Preparation of (1S,3aS,5aR,5bR,7aS,11aS, 11bS,13aR,13bR)-benzyl 11-fluoro-1-isopropyl-9-(4-(methoxycarbonyl)phenyl)-5a,5b,8,8,11a-pentamethyl-2,3,3a,4,5,5a,5b,6,7,7a,8,11,11a,11b,12,13,13a, 13b-octadecahydro-1H-cyclopenta[a]chrysene-3a-carboxylate To a solution of (1S,3aS,5aR,5bR,7aS,11aS,11bS,13aR, 13bR)-benzyl 11-hydroxy-1-isopropyl-9-(4-(methoxycarbonyl)phenyl)-5a,5b,8,8,11a-pentamethyl-2,3,3a,4,5,5a,5b,6, 7,7a,8,11,11a,11b,12,13,13a,13b-octadecahydro-1H-cyclopenta[a]chrysene-3a-carboxylate (45 mg, 0.066 mmol) in dichloromethane (2 mL) at −30° C. was added pyridine (10.72 μL, 0.133 mmol), then diethylaminosulfur trifluoride (0.026 mL, 0.199 mmol) was added. The reaction mixture was slowly warmed up to 0° C. and stirred for 3 h. The reaction mixture was quenched with distilled water (5 mL) and extracted with dichloromethane (3×4 mL), the extracts were combined, dried over sodium sulfate, filtered and concentrated under reduced pressure. The residue was purified by flash chromatography with 0-30% ethyl acetate/ hexanes to give the title compound as clear oil. (39 mg, 84%). $^1$H NMR (400 MHz, CHLOROFORM-d) δ 7.97 (d, J=8.3 Hz, 2H), 7.49-7.34 (m, 5H), 7.22 (d, J=8.3 Hz, 2H), 5.57 (dd, J=6.0, 2.0 Hz, 1H), 5.18-5.09 (m, 2H), 4.61-4.47 (m, 1H), 3.93 (s, 3H), 2.43-0.83 (m, 22H), 1.03 (s, 3H), 0.98-0.85 (m, 15H), 0.77 (d, J=6.8 Hz, 3H).

Step 2. Preparation of (1S,3aS,5aR,5bR,7aS,11aS, 11bS,13aR,13bR)-benzyl 11-fluoro-1-isopropyl-9-(4-(methoxycarbonyl)phenyl)-5a,5b,8,8,11a-pentamethyl-2,3,3a,4,5,5a,5b,6,7,7a,8,11,11a,11b,12,13,13a, 13b-octadecahydro-1H-cyclopenta[a]chrysene-3a-carboxylate A mixture of (1S,3aS,5aR,5bR,7aS,11aS,11bS,13aR, 13bR)-benzyl 11-fluoro-1-isopropyl-9-(4-(methoxycarbonyl)phenyl)-5a,5b,8,8,11a-pentamethyl-2,3,3a,4,5,5a,5b,6, 7,7a,8,11,11a,11b,12,13,13a,13b-octadecahydro-1H-cyclopenta[a]chrysene-3a-carboxylate (40 mg, 0.057 mmol), palladium acetate (2.6 mg, 0.011 mmol), triethylamine (0.024 mL, 0.172 mmol) and tert-butyldimethylsilane (19.99 mg, 0.172 mmol) in dichloroethane (1 mL) was heated up at 60° C. for 3 h. The reaction mixture was filtered through a pad of celite, then concentrated under reduced pressure to provide the silyl ester intermediate. To this intermediate in dioxane (1 mL) was added TBAF (0.229 mL, 0.229 mmol) and the reaction mixture was stirred for 3 h at room temperature. To the reaction mixture was added 2 mL distilled water. A white precipitate was observed, collected and dried to provide the title compound (30 mg, 88%). LCMS: m/e 591.4 (M-H)$^-$, 3.05 min (method 2).

Step 3. A mixture of (1S,3aS,5aR,5bR,7aS,11aS,11bS, 13aR,13bR)-benzyl 11-fluoro-1-isopropyl-9-(4-(methoxycarbonyl)phenyl)-5a,5b,8,8,11a-pentamethyl-2,3,3a,4,5,5a, 5b,6,7,7a,8,11,11a,11b,12,13,13a,13b-octadecahydro-1H-cyclopenta[a]chrysene-3a-carboxylate (30 mg, 0.049 mmol) and oxalyl dichloride (0.247 mL, 0.494 mmol) in dichloromethane (1 mL) was stirred at rt for 3 h. The reaction mixture was concentrated under reduced pressure to provide the corresponding acid chloride.

To a solution of 4-(3-aminopropyl)thiomorpholine 1,1-dioxide (13.78 mg, 0.072 mmol), Hunig's Base (0.025 mL, 0.143 mmol) and DMAP (0.584 mg, 4.78 µmol) in dichloromethane (1 mL) was added a solution of the acid chloride from above in dichloromethane (1 mL). The reaction mixture was stirred at 20° C. for 3 h. The reaction mixture was quenched with distilled water (3 mL) and extracted with dichloromethane (3×4 mL). All the extracts were combined, dried over sodium sulfate, filtered and concentrated under reduced pressure to provide 38 mg of a mixture of methyl 4-((1S,3aS,5aR,5bR,7aS,11aS,11bS,13aR,13bR)-11-chloro-3a-((3-(1,1-dioxidothiomorpholino)propyl)carbamoyl)-1-isopropyl-5a,5b,8,8,11a-pentamethyl-2,3,3a,4,5,5a,5b,6,7, 7a,8,11,11a,11b,12,13,13a,13b-octadecahydro-1H-cyclopenta[a]chrysen-9-yl)benzoate, LCMS: m/e 783.4 (M+H)$^+$, 2.88 min (method 2) and methyl 4-((1S,3aS,5aR, 5bR,7aS,11aS,11bS,13aR,13bR)-3a-((3-(1,1-dioxidothiomorpholino)propyl)carbamoyl)-11-fluoro-1-isopropyl-5a, 5b,8,8,11a-pentamethyl-2,3,3a,4,5,5a,5b,6,7,7a,8,11,11a, 11b,12,13,13a,13b-octadecahydro-1H-cyclopenta[a]chrysen-9-yl)benzoate, LCMS: m/e 765.4 (M-H)$^-$, 2.75 min (method 2).

Step 4. The mixture of methyl 4-((1S,3aS,5aR,5bR,7aS, 11aS,11bS,13aR,13bR)-11-chloro-3a-((3-(1,1-dioxidothiomorpholino)propyl)carbamoyl)-1-isopropyl-5a,5b,8,8,11a-pentamethyl-2,3,3a,4,5,5a,5b,6,7,7a,8,11,11a,11b,12,13, 13a,13b-octadecahydro-1H-cyclopenta[a]chrysen-9-yl) benzoate and methyl 4-((1S,3aS,5aR,5bR,7aS,11aS,11bS, 13aR,13bR)-3a-((3-(1,1-dioxidothiomorpholino)propyl) carbamoyl)-11-fluoro-1-isopropyl-5a,5b,8,8,11a-pentamethyl-2,3,3a,4,5,5a,5b,6,7,7a,8,11,11a,11b,12,13, 13a,13b-octadecahydro-1H-cyclopenta[a]chrysen-9-yl) benzoate sodium hydroxide from above (38 mg) in dioxane (1 mL) was treated with 1N NaOH (0.6 mL) and heated up at 78° C. for 3 h. The reaction mixture was filtered and the clear solution was purified by HPLC to provide Example 7: 4-((1S,3aS,5aR,5bR,7aS,11S,11aS,11bS,13aR,13bR)-3a-((3-(1,1-dioxidothiomorpholino)propyl)carbamoyl)-11-hydroxy-1-isopropyl-5a,5b,8,8,11a-pentamethyl-2,3,3a,4,5,5a, 5b,6,7,7a,8,11,11a,11b,12,13,13a,13b-octadecahydro-1H-cyclopenta[a]chrysen-9-yl)benzoic acid as a white solid (8.2 mg, 23%). LCMS: m/e 751.4 (M+H)$^+$, 2.13 min (method 2). $^1$H NMR (400 MHz, Acetic) δ 8.01 (d, J=8.3 Hz, 2H), 7.28 (d, J=8.3 Hz, 2H), 5.58 (d, J=6.0 Hz, 1H), 3.89 (d, J=6.3 Hz, 1H), 3.80 (br. s., 4H), 3.55 (br. s., 4H), 3.45-3.28 (m, 2H), 3.24 (dd, J=9.8, 5.8 Hz, 2H), 2.53 (td, J=12.0, 2.6 Hz, 1H), 2.39-1.16 (m, 23H), 1.06 (s, 3H), 1.04 (s, 3H), 1.00 (s, 3H), 0.98 (s, 3H), 0.97 (s, 3H), 0.87 (d, J=6.8 Hz, 3H), 0.79 (d, J=6.8 Hz, 3H) and Example 8: 4-((1S,3aS,5aR,5bR,7aS, 11R,11aS,11bS,13aR,13bR)-3a-((3-(1,1-dioxidothiomorpholino)propyl)carbamoyl)-11-fluoro-1-isopropyl-5a,5b,8, 8,11a-pentamethyl-2,3,3a,4,5,5a,5b,6,7,7a,8,11,11a,11b,12, 13,13a,13b-octadecahydro-1H-cyclopenta[a]chrysen-9-yl) benzoic acid as a white solid (1.1 mg, 43%). LCMS: m/e 753.4 (M+H)$^+$, 2.39 min (method 2). $^1$H NMR (400 MHz, Acetic) δ 8.03 (d, J=8.3 Hz, 2H), 7.29 (d, J=8.3 Hz, 2H), 5.25 (d, J=18.3 Hz, 1H), 5.02-4.81 (m, 1H), 3.82 (br. s., 4H), 3.58 (br. s., 4H), 3.48-3.18 (m, 4H), 2.58-1.14 (m, 24H), 1.11 (d, J=2.3 Hz, 3H), 1.05 (s, 3H), 1.03 (s, 3H), 1.01 (s, 3H), 0.95 (s, 3H), 0.87 (d, J=6.8 Hz, 3H), 0.78 (d, J=6.5 Hz, 3H).

Example 9

Preparation of 4-((1S,3aS,5aR,5bR,7aS,11aS,11bS, 13aR,13bR)-3a-amino-1-isopropyl-5a,5b,8,8,11a-pentamethyl-11-oxo-2,3,3a,4,5,5a,5b,6,7,7a,8,11, 11a,11b,12,13,13a,13b-octadecahydro-1H-cyclopenta[a]chrysen-9-yl)benzoic acid

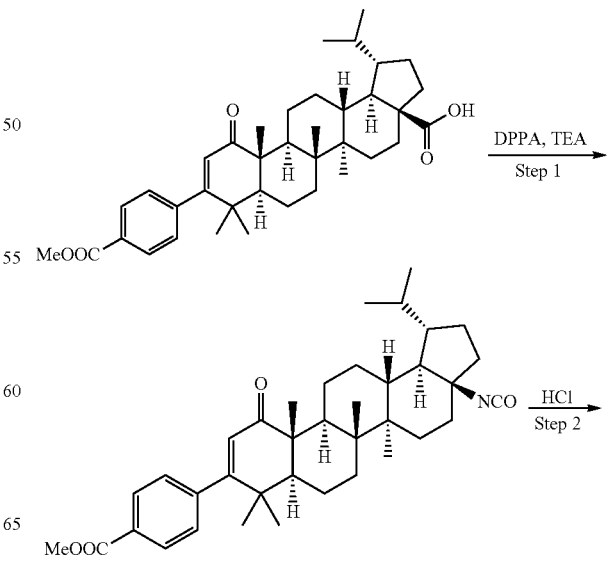

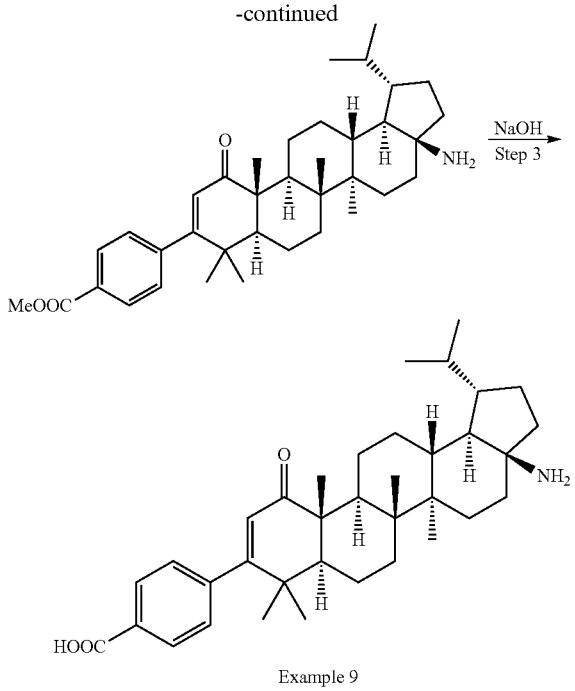

Example 9

Step 1. Preparation of methyl 4-((1S,3aS,5aR,5bR, 7aS,11aS,11bS,13aR,13bR)-3a-isocyanato-1-isopropyl-5a,5b,8,8,11a-pentamethyl-11-oxo-2,3,3a,4,5,5a, 5b,6,7,7a,8,11,11a,11b,12,13,13a,13b-octadecahydro-1H-cyclopenta[a]chrysen-9-yl)benzoate A mixture of (1S,3aS,5aR,5bR,7aS,11aS,11bS,13aR, 13bR)-1-isopropyl-9-(4-(methoxycarbonyl)phenyl)-5a,5b, 8,8,11a-pentamethyl-11-oxo-2,3,3a,4,5,5a,5b,6,7,7a,8,11, 11a,11b,12,13,13a,13b-octadecahydro-1H-cyclopenta[a] chrysene-3a-carboxylic acid (150 mg, 0.255 mmol), diphenyl phosphorazidate (60.7 µl, 0.280 mmol) and triethylamine (107 µl, 0.764 mmol) in dioxane (5 mL) was refluxed at 100° C. for 16 h. The reaction mixture was concentrated under reduced pressure and the residue was purified by flash chromatography with 0-30% ethyl acetate/hexanes to provide the desired final product as a white solid. (90 mg, 60%). LCMS: m/e 586.6 (M+H)+, 3.24 min (method 1).

Step 2. Preparation of methyl 4-((1S,3aS,5aR,5bR, 7aS,11aS,11bS,13aR,13bR)-3a-amino-1-isopropyl-5a,5b,8,8,11a-pentamethyl-11-oxo-2,3,3a,4,5,5a,5b, 6,7,7a,8,11,11a,11b,12,13,13a,13b-octadecahydro-1H-cyclopenta[a]chrysen-9-yl)benzoate A mixture of methyl 4-((1S,3aS,5aR,5bR,7aS,11aS,11bS, 13aR,13bR)-3a-isocyanato-1-isopropyl-5a,5b,8,8,11a-pentamethyl-11-oxo-2,3,3a,4,5,5a,5b,6,7,7a,8,11,11a,11b,12, 13,13a,13b-octadecahydro-1H-cyclopenta[a]chrysen-9-yl) benzoate (90 mg, 0.154 mmol) and conc. HCl (0.133 mL, 1.536 mmol) in THF (5 mL) was stirred at 20° C. for 13 h. The reaction mixture was concentrated under reduced pressure to provide the desired product as a white solid. (80 mg, 93%). LCMS: m/e 560.7 (M+H)+, 1.90 min (method 1).

Step 3. A mixture of methyl 4-((1S,3aS,5aR,5bR,7aS, 11aS,11bS,13aR,13bR)-3a-amino-1-isopropyl-5a,5b,8,8, 11a-pentamethyl-11-oxo-2,3,3a,4,5,5a,5b,6,7,7a,8,11,11a, 11b,12,13,13a,13b-octadecahydro-1H-cyclopenta[a] chrysen-9-yl)benzoate (5 mg, 8.93 µmol) and 1N sodium hydroxide (0.089 mL, 0.089 mmol) in dioxane (1 mL) was heated up at 80° C. for 3 h. The reaction mixture was filtered and purified by prep. HPLC with 0-70 acetonitrile/water/TFA to provide 4-((1S,3aS,5aR,5bR,7aS,11aS,11bS,13aR, 13bR)-3a-amino-1-isopropyl-5a,5b,8,8,11a-pentamethyl-11-oxo-2,3,3a,4,5,5a,5b,6,7,7a,8,11,11a,11b,12,13,13a,13b-octadecahydro-1H-cyclopenta[a]chrysen-9-yl)benzoic acid as colorless oil (2.8 mg, 55%). LCMS: m/e 546.6 (M+H)+, 1.67 min (method 2). $^1$H NMR (500 MHz, CHLOROFORM-d) δ8.08 (d, J=8.4 Hz, 2H), 7.29 (d, J=8.2 Hz, 2H), 5.64 (s, 1H), 2.17-0.98 (m, 22H), 1.38 (s, 3H), 1.21 (s, 3H), 1.20 (s, 3H), 1.08 (s, 3H), 1.05 (s, 3H), 0.93 (d, J=6.8 Hz, 3H), 0.84 (d, J=6.8 Hz, 3H).

Example 10

Preparation of 4-((1S,3aS,5aR,5bR,7aS,11aS,11bS, 13aR,13bR)-3a-((2-(1,1-dioxidothiomorpholino) ethyl)amino)-1-isopropyl-5a,5b,8,8,11a-pentamethyl-11-oxo-2,3,3a,4,5,5a,5b,6,7,7a,8,11,11a,11b, 12,13,13a,13b-octadecahydro-1H-cyclopenta[a] chrysen-9-yl)benzoic acid

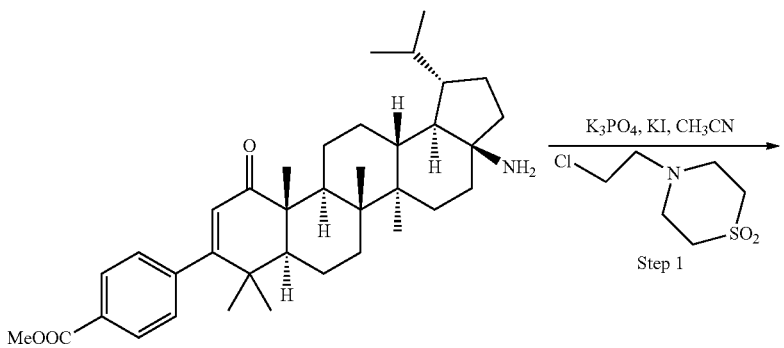

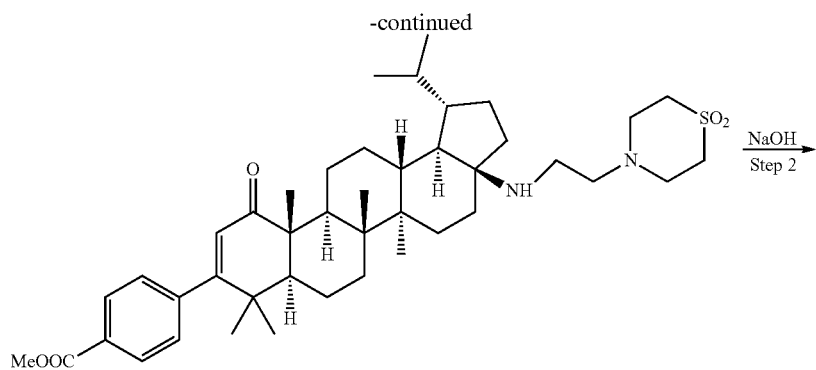

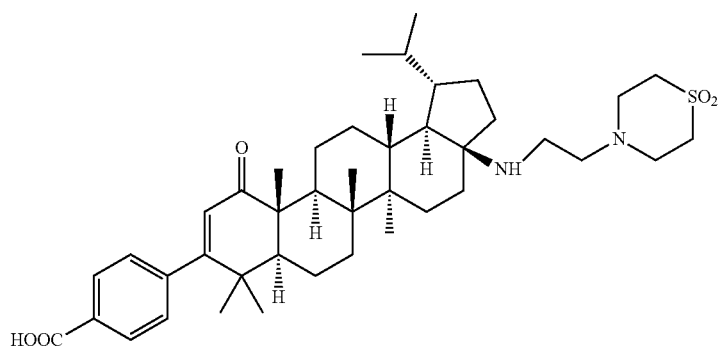

Example 10

Step 1. Preparation of methyl 4-((1S,3aS,5aR,5bR,7aS,11aS,11bS,13aR,13bR)-3a-((2-(1,1-dioxidothiomorpholino)ethyl)amino)-1-isopropyl-5a,5b,8,8,11a-pentamethyl-11-oxo-2,3,3a,4,5,5a,5b,6,7,7a,8,11,11a,11b,12,13,13a,13b-octadecahydro-1H-cyclopenta[a]chrysen-9-yl)benzoate A mixture of methyl 4-((1S,3aS,5aR,5bR,7aS,11aS,11bS,13aR,13bR)-3a-amino-1-isopropyl-5a,5b,8,8,11a-pentamethyl-11-oxo-2,3,3a,4,5,5a,5b,6,7,7a,8,11,11a,11b,12,13,13a,13b-octadecahydro-1H-cyclopenta[a]chrysen-9-yl)benzoate (20 mg, 0.036 mmol), 4-(2-chloroethyl)thiomorpholine 1,1-dioxide (14.12 mg, 0.071 mmol), potassium phosphate (30.3 mg, 0.143 mmol) and potassium iodide (7.71 mg, 0.046 mmol) in acetonitrile (2 mL) was heated up for 18 h at 110° C. The reaction mixture was filtered and purified by prep. HPLC with 0-70 acetonitrile/water/TFA to provide the desired product as a white solid. (13 mg, 51%). LCMS: m/e 721.7 (M+H)⁺, 1.88 min (method 1).

Step 2. A mixture of methyl 4-((1S,3aS,5aR,5bR,7aS,11aS,11bS,13aR,13bR)-3a-((2-(1,1-dioxidothiomorpholino)ethyl)amino)-1-isopropyl-5a,5b,8,8,11a-pentamethyl-11-oxo-2,3,3a,4,5,5a,5b,6,7,7a,8,11,11a,11b,12,13,13a,13b-octadecahydro-1H-cyclopenta[a]chrysen-9-yl)benzoate (13 mg, 0.018 mmol) and 1N sodium hydroxide (0.180 mL, 0.180 mmol) in dioxane (1 mL) was heated up at 80° C. for 3 h. The reaction mixture was filtered and purified by prep. HPLC with 0-70 acetonitrile/water/TFA to provide 4-((1S,3aS,5aR,5bR,7aS,11aS,11bS,13aR,13bR)-3a-((2-(1,1-dioxidothiomorpholino)ethyl)amino)-1-isopropyl-5a,5b,8,8,11a-pentamethyl-11-oxo-2,3,3a,4,5,5a,5b,6,7,7a,8,11,11a,11b,12,13,13a,13b-octadecahydro-1H-cyclopenta[a]chrysen-9-yl)benzoic acid as colorless oil (4.1 mg, 32%). LCMS: m/e 707.7 (M+H)⁺, 1.60 min (method 1). ¹H NMR (500 MHz, ACETONITRILE-d₃) δ 8.01 (d, J=8.4 Hz, 2H), 7.36 (d, J=8.4 Hz, 2H), 5.54 (s, 1H), 3.41-2.81 (m, 12H), 2.35-1.34 (m, 22H), 1.39 (s, 3H), 1.27 (s, 3H), 1.21 (s, 3H), 1.09 (s, 3H), 1.04 (s, 3H), 0.92 (d, J=6.9 Hz, 3H), 0.87 (d, J=6.8 Hz, 3H).

Example 11
Preparation of (1S,3aS,5aR,5bR,7aR,8aS,9aS,10aR,10bR,12aR,12bR)-8a-(4-carboxyphenyl)-1-isopropyl-5a,5b,8,8,10a-pentamethylicosahydro-1H-cyclopenta[7,8]chryseno[2,3-b]oxirene-3a-carboxylic acid
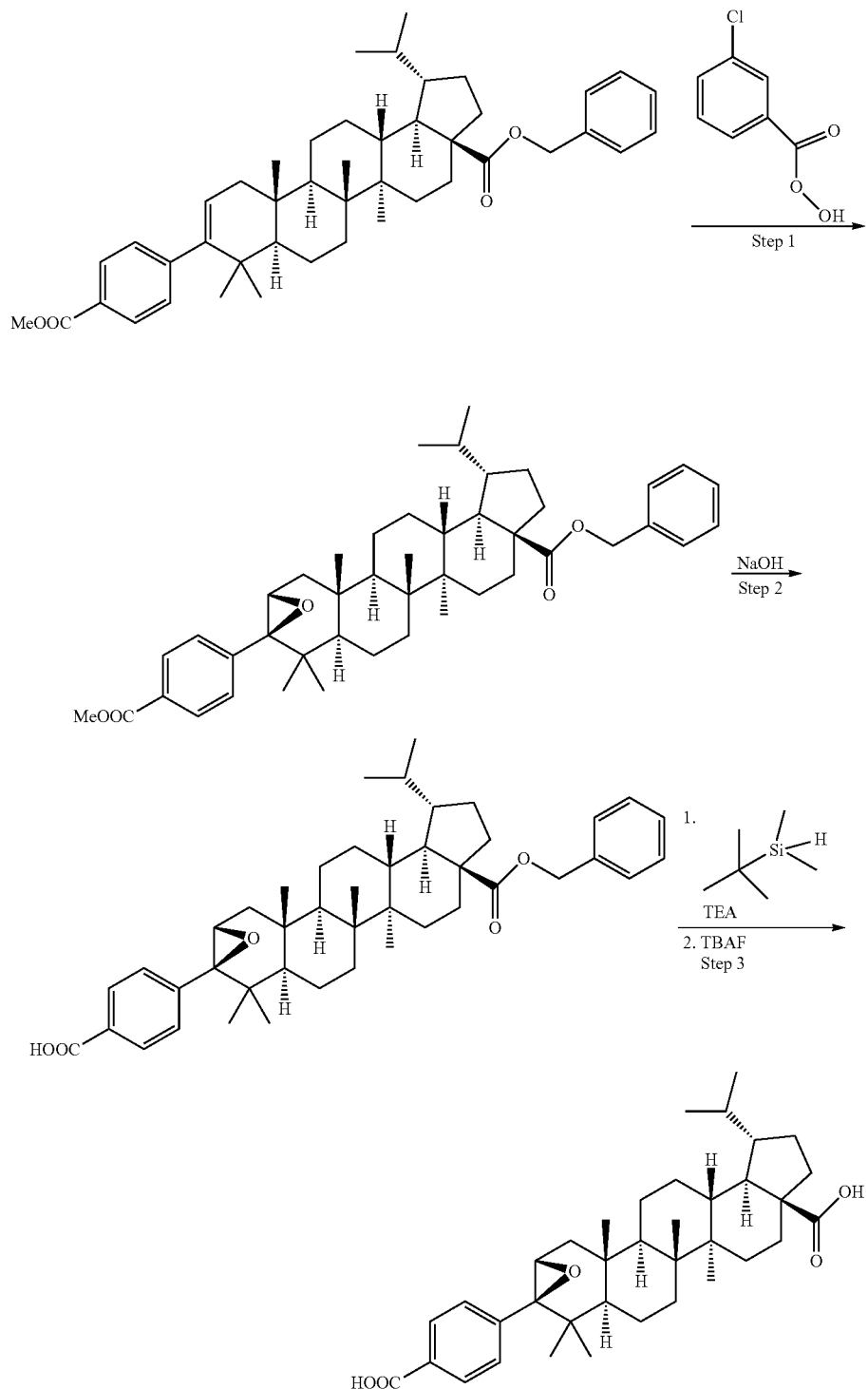
Example 11

Step 1. Preparation of (1S,3aS,5aR,5bR,7aR,8aS, 9aS,10aR,10bR,12aR,12bR)-benzyl 1-isopropyl-8a-(4-(methoxycarbonyl)phenyl)-5a,5b,8,8,10a-pentamethylicosahydro-1H-cyclopenta[7,8]chryseno[2,3-b]oxirene-3a-carboxylate To a mixture of (1S,3aS,5aR,5bR,7aR,11aS,11bR,13aR,13bR)-benzyl 1-isopropyl-9-(4-(methoxycarbonyl)phenyl)-5a,5b,8,8,11a-pentamethyl-2,3,3a,4,5,5a,5b,6,7,7a,8,11,11a,11b,12,13,13a,13b-octadecahydro-1H-cyclopenta[a]chrysene-3a-carboxylate (27 mg, 0.041 mmol) in dichloromethane (1 mL) at −78° C. was added 3-chlorobenzoperoxoic acid (27.3 mg, 0.122 mmol) and the mixture was stirred for 3 h at −78° C. The reaction mixture was quenched with distilled water (3 mL) and extracted with dichloromethane (3×4 mL). All the extracts were combined, dried over sodium sulfate, filtered and concentrated under reduced pressure to provide the title compound as a white solid (20 mg, 72%). LCMS: m/e 681.4 (M+H)$^+$, 3.37 min (method 2).

Step 2. Preparation of 4-((1S,3aS,5aR,5bR,7aR,8aS, 9aS,10aR,10bR,12aR,12bR)-3a-((benzyloxy)carbonyl)-1-isopropyl-5a,5b,8,8,10a-pentamethylicosahydro-1H-cyclopenta[7,8]chryseno[2,3-b]oxiren-8a-yl)benzoic acid A mixture of (1S,3aS,5aR,5bR,7aR,8aS,9aS,10aR,10bR,12aR,12bR)-benzyl 1-isopropyl-8a-(4-(methoxycarbonyl)phenyl)-5a,5b,8,8,10a-pentamethylicosahydro-1H-cyclopenta[7,8]chryseno[2,3-b]oxirene-3a-carboxylate (20 mg, 0.030 mmol) and sodium hydroxide (0.150 mL, 0.150 mmol) in dioxane (1 mL) was heated up at 78° C. for 3 h. The reaction mixture was quenched with distilled water (3 mL) and extracted with dichloromethane (3×2 mL). All the extracts were combined, dried over sodium sulfate, filtered and concentrated under reduced pressure to provide the desired product as a white solid (15 mg, 75%). LCMS: m/e 667.3 (M+H)$^+$, 2.37 min (method 1).

Step 3. A mixture of 4-((1S,3aS,5aR,5bR,7aR,8aS,9aS,10aR,10bR,12aR,12bR)-3a-((benzyloxy)carbonyl)-1-isopropyl-5a,5b,8,8,10a-pentamethylicosahydro-1H-cyclopenta[7,8]chryseno[2,3-b]oxiren-8a-yl)benzoic acid (15 mg, 0.022 mmol), tert-butyldimethylsilane (5.23 mg, 0.045 mmol), TEA (5.02 μL, 0.036 mmol) and palladium acetate (1.262 mg, 5.62 μmol) in dichloroethane (1 mL) in a seal tube was heated up at 60° C. for 2 hours. The reaction mixture was filtered through a pad of celite, then concentrated under reduced pressure to provide the intermediate as yellow oil. To this intermediate in dioxane (1 mL) was added TBAF (20.18 mg, 0.058 mmol), the reaction mixture was stirred at room temperature for 3 hours. The reaction mixture was purified by HPLC to provide the desired product as white solid (4 mg, 46%). LCMS: m/e 575.3 (M−H)$^−$, 2.18 min (method 2). $^1$H NMR (500 MHz, Acetic) δ 8.07 (d, J=8.2 Hz, 2H), 7.52 (d, J=8.5 Hz, 2H), 3.27 (d, J=6.1 Hz, 1H), 2.55-1.17 (m, 24H), 1.15 (s, 3H), 1.14 (s, 3H), 1.05 (s, 3H), 1.02 (s, 3H), 0.92 (d, J=6.7 Hz, 3H), 0.87 (s, 3H), 0.84 (d, J=6.7 Hz, 3H).

HIV Cell Culture Assay—

MT-2 cells and 293T cells were obtained from the NIH AIDS Research and Reference Reagent Program. MT-2 cells were propagated in RPMI 1640 media supplemented with 10% heat inactivated fetal bovine serum, 100 μg/mL penicillin G and up to 100 units/mL streptomycin. The 293T cells were propagated in DMEM media supplemented with 10% heat inactivated fetal bovine serum (FBS), 100 units/mL penicillin G and 100 μg/mL streptomycin. The proviral DNA clone of NL$_{4-3}$ was obtained from the NIH AIDS Research and Reference Reagent Program. A recombinant NL$_{4-3}$ virus, in which a section of the nef gene from NL4-3 was replaced with the *Renilla* luciferase gene, was used as a reference virus. In addition, residue Gag P373 was converted to P373S. Briefly, the recombinant virus was prepared by transfection of the altered proviral clone of NL$_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) μL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The EC$_{50}$ data for the compounds is shown in Table 1.

TABLE 1

| Example # | Structure | (EC50, uM) |
|---|---|---|
| 1 | 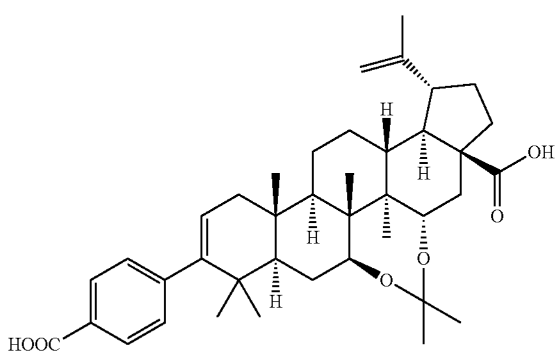 | 0.04 |

TABLE 1-continued

| Example # | Structure | (EC50, uM) |
|---|---|---|
| 2 | 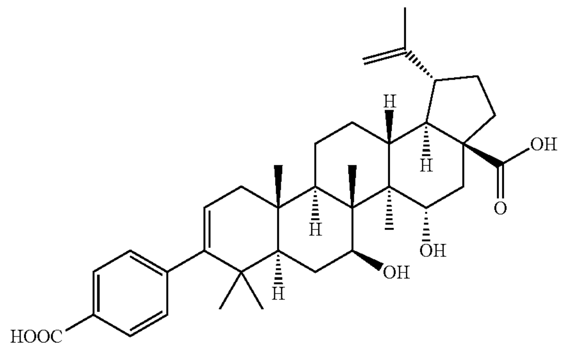 | 1.56 |
| 3 | 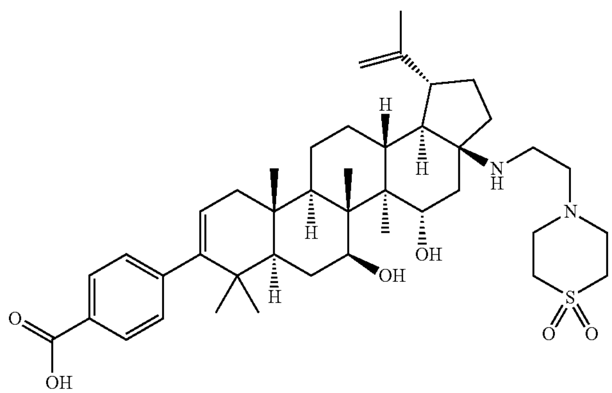 | 0.017 |
| 4 | 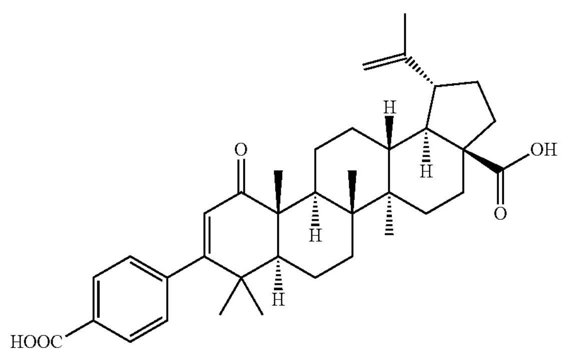 | 0.029 |
| 5 | 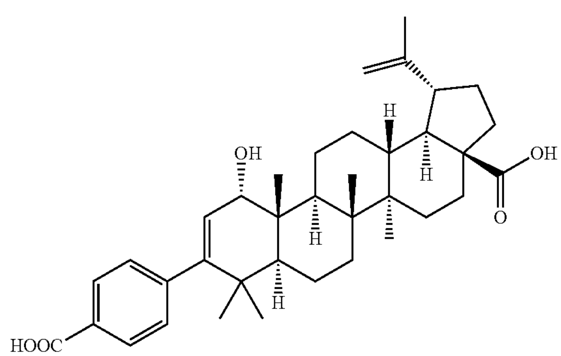 | 0.41 |

TABLE 1-continued

| Example # | Structure | (EC50, uM) |
|---|---|---|
| 6 | 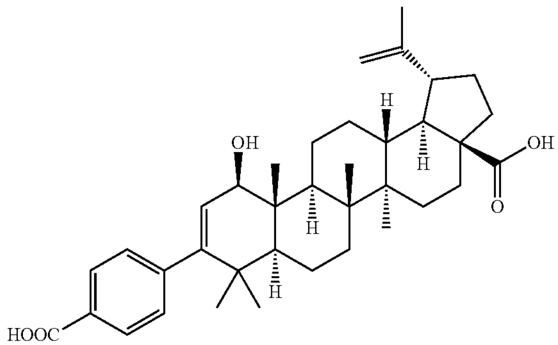 | 1.73 |
| 7 | 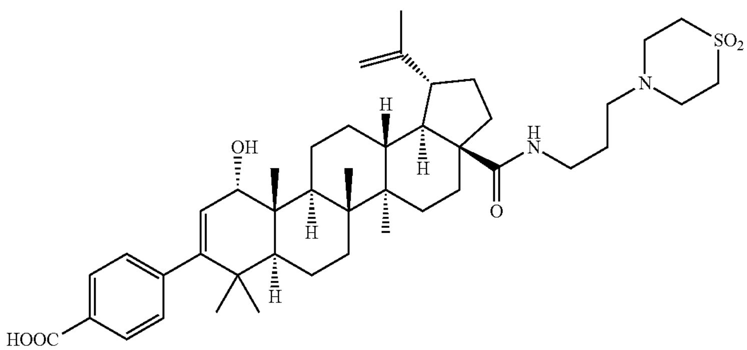 | 2.67E−03 |
| 8 | 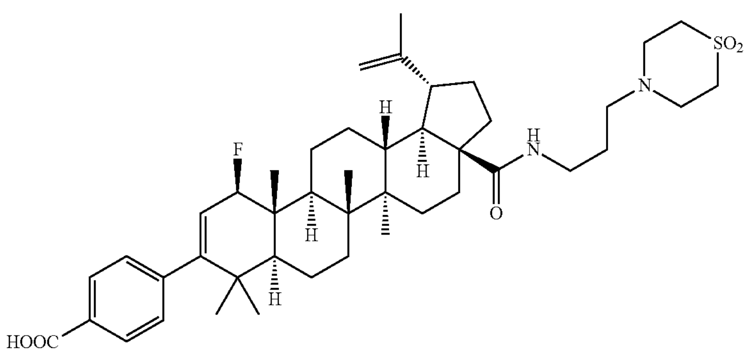 | 3.31E−03 |
| 9 | 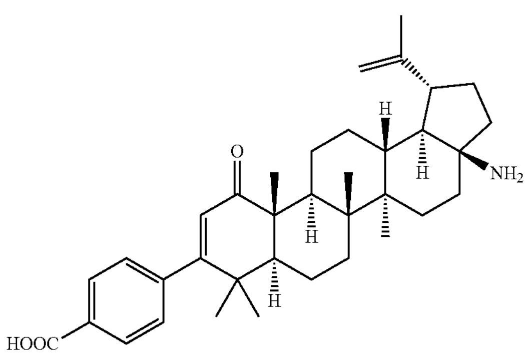 | 0.0012 |

TABLE 1-continued

| Example # | Structure | (EC50, uM) |
|---|---|---|
| 10 | 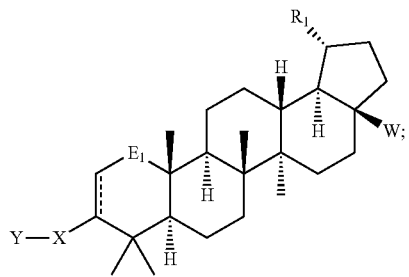 | 0.0012 |
| 11 | 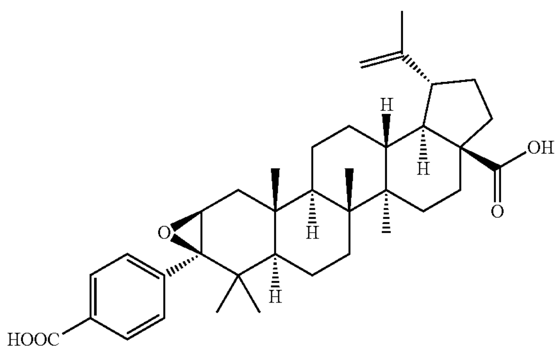 | 1.31 |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound, including pharmaceutically acceptable salts thereof, which is selected from the group of:

a compound of formula I

Formula I a compound of formula II

Formula II

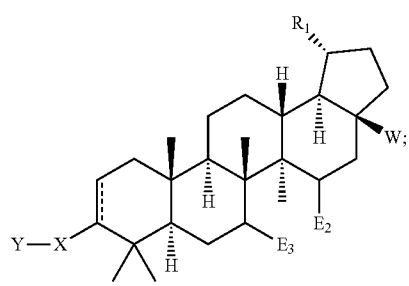

and a compound of formula III

Formula III

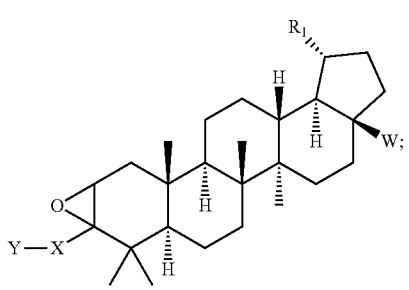

wherein $R_1$ is isopropenyl or isopropyl;
$E_1$ is selected from the group of —$CHOR_{22}$, —CO, —CHF and —$CF_2$;

$E_2$ and $E_3$ are selected from —CHOR$_{22}$ and F; or
$E_2$ and $E_3$ can together form a ketal such as:

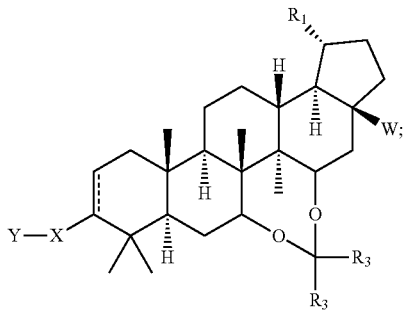

wherein X is selected from the group of phenyl, heteroaryl ring, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl and $C_6$ cyclodialkenyl;

X is substituted with A, wherein A is at least one member selected from the group of —H, -halo, -hydroxyl, —$C_{1-6}$ alkyl, —$C_{1-6}$ alkoxy, —$C_{1-6}$ haloalkyl, —NR$_2$R$_2$, —COOR$_2$, and —C(O)NR$_2$R$_2$, wherein R$_2$ is selected from the group of —H, —$C_{1-6}$ alkyl, -alkylsubstituted $C_{1-6}$ alkyl, and -arylsubstituted $C_{1-6}$ alkyl;

Y is selected from the group of —COOR$_2$, —C(O)NR$_2$SO$_2$R$_3$, —$C_{3-6}$ cycloalkyl-COOR$_2$, —$C_{1-6}$ alkyl-COOR$_2$, -alkylsubstituted $C_{1-6}$ alkyl-COOR$_2$, —SO$_2$NR$_2$C(O)R$_2$, and tetrazole, R$_3$ is —$C_{1-6}$ alkyl or -alkylsubstituted $C_{1-6}$ alkyl;

W is —COOR$_2$, —(CH$_2$)$_{0-1}$NR$_4$R$_5$, or —CONR$_{20}$R$_{21}$;

R$_4$ is selected from the group of —H, —$C_{1-6}$ alkyl, —$C_{1-6}$ alkyl-C(OR$_3$)$_2$-$C_{3-6}$ cycloalkyl, —$C_{1-6}$ substituted alkyl, —$C_{1-6}$ alkyl-$C_{3-6}$ cycloalkyl, —$C_{1-6}$ alkyl-Q$_1$, —$C_{1-6}$ alkyl-$C_{3-6}$ cycloalkyl-Q$_1$, -aryl, -heteroaryl, substituted heteroaryl, —COR$_6$, —COCOR$_6$, —SO$_2$R$_7$, and —SO$_2$NR$_2$R$_2$, wherein Q$_1$ is selected from the group of -heteroaryl, substituted heteroaryl, -halogen, —CF$_3$, —OR$_2$, —COOR$_2$, —NR$_8$R$_9$, —CONR$_{10}$R$_{11}$ and —SO$_2$R$_7$;

R$_5$ is selected from the group of —H, —$C_{1-6}$ alkyl, —$C_{3-6}$ cycloalkyl, —$C_{1-6}$ alkylsubstituted alkyl, —$C_{1-6}$ alkyl-NR$_8$R$_9$, —COR$_{10}$, —COR$_6$, —COCOR$_6$, —SO$_2$R$_7$ and —SO$_2$NR$_2$R$_2$;

with the proviso that only one of R$_4$ or R$_5$ can be selected from the group of —COR$_6$, —COCOR$_6$, —SO$_2$R$_7$ and —SO$_2$NR$_2$R$_2$;

R$_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-Q$_2$, —$C_{1-6}$ alkyl-Q$_2$, —$C_{1-6}$ alkyl-substitutedalkyl-Q$_2$, —$C_{3-6}$ cycloalkyl-Q$_2$, aryl-Q$_2$, —NR$_{13}$R$_{14}$, and —OR$_{15}$;

wherein Q$_2$ is selected from the group of -aryl, -heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

R$_7$ is selected from the group of —$C_{1-6}$ alkyl, —$C_{1-6}$ substituted alkyl, —$C_{3-6}$ cycloalkyl, aryl, and -heteroaryl;

R$_8$ and R$_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-Q$_2$, and —COOR$_3$, or R$_8$ and R$_9$ are taken together with the adjacent N to form a cycle selected from the group of:

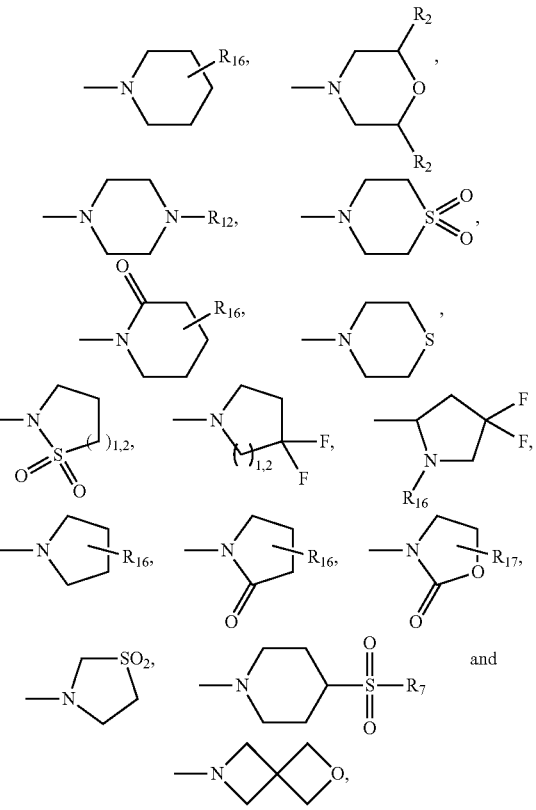

with the proviso that only one of R$_8$ or R$_9$ can be —COOR$_3$;

R$_{10}$ and R$_{11}$ are independently selected from the group of —H, —$C_{1-6}$ alkyl, —$C_{1-6}$ substituted alkyl and —$C_{3-6}$ cycloalkyl;

R$_{12}$ is selected from the group of —$C_{1-6}$ alkyl, —$C_{1-6}$ alkyl-OH; —$C_{1-6}$ alkyl, —$C_{1-6}$ substituted alkyl, —$C_{3-6}$ cycloalkyl, and —COR$_7$;

R$_{13}$ and R$_{14}$ are independently selected from the group of —H, —$C_{1-6}$ alkyl, —$C_{3-6}$ cycloalkyl, —$C_{1-6}$ substituted alkyl, —$C_{1-6}$ alkyl-Q$_3$, —$C_{1-6}$ alkyl-$C_{3-6}$ cycloalkyl-Q$_3$, and $C_{1-6}$ substituted alkyl-Q$_3$;

Q$_3$ is selected from the group of -heteroaryl, substituted heteroaryl, —NR$_{18}$R$_{19}$, —CONR$_2$R$_2$, —COOR$_2$, —OR$_2$, and —SO$_2$R$_3$;

R$_{15}$ is selected from the group of —$C_{1-6}$ alkyl, —$C_{3-6}$ cycloalkyl, —$C_{1-6}$ substituted alkyl, —$C_{1-6}$ alkyl-Q$_3$, —$C_{1-6}$ alkyl-$C_{3-6}$ cycloalkyl-Q$_3$ and —$C_{1-6}$ substituted alkyl-Q$_3$;

R$_{16}$ is selected from the group of —H, —$C_{1-6}$ alkyl, —NR$_2$R$_2$, and —COOR$_3$;

R$_{17}$ is selected from the group of —H, —$C_{1-6}$ alkyl, —COOR$_3$, and -aryl;

R$_{18}$ and R$_{19}$ are independently selected from the group of —H, —$C_{1-6}$ alkyl, —$C_{1-6}$ substituted alkyl, —$C_{1-6}$ substituted alkyl-OR$_2$, and —COR$_3$;

R$_{20}$ and R$_{21}$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-Q$_2$, and —COOR$_3$, or R$_{20}$ and R$_{21}$ are taken together with the adjacent N to form a cycle selected from the group of:

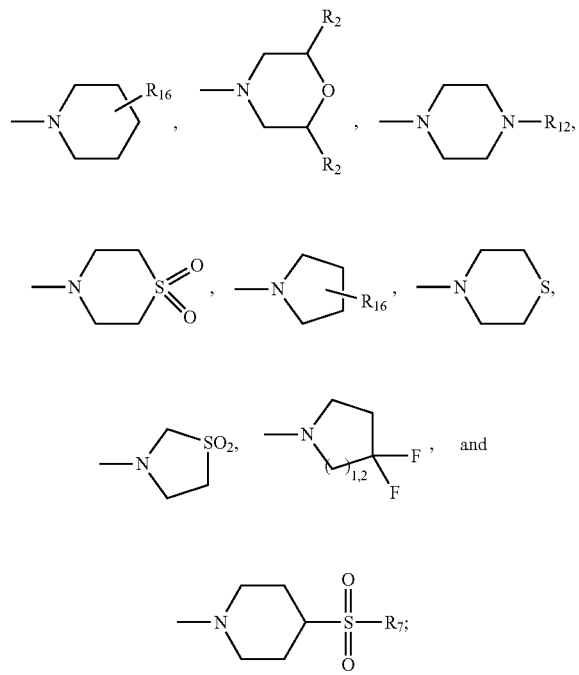

and

R$_{22}$ is selected from H and —COR$_3$.

2. The compound as claimed in claim 1, wherein X is phenyl.

3. The compound as claimed in claim 2, wherein Y is —COOH.

4. The compound as claimed in claim 3, wherein said compound has the Formula I.

5. The compound as claimed in claim 4, wherein E$_1$ is —CHOR$_{22}$.

6. The compound as claimed in claim 5, wherein E$_1$ is —CHOH.

7. The compound as claimed in claim 4, wherein E$_1$ is —CO.

8. The compound as claimed in claim 4, wherein E$_1$ is —CHF.

9. The compound as claimed in claim 3, wherein said compound has the Formula II.

10. The compound as claimed in claim 9, wherein E$_2$ and E$_3$ are each —CHOR$_{22}$.

11. The compound as claimed in claim 9, wherein E$_2$ and E$_3$ together form said ketal.

12. The compound as claimed in claim 11, wherein R$_3$ is methyl.

13. The compound as claimed in claim 3, wherein said compound has the Formula III.

14. The compound as claimed in claim 1, wherein W is —(CH$_2$)$_{0-1}$NR$_4$R$_5$.

15. A compound, including pharmaceutically acceptable salts thereof, which is selected from the group of:

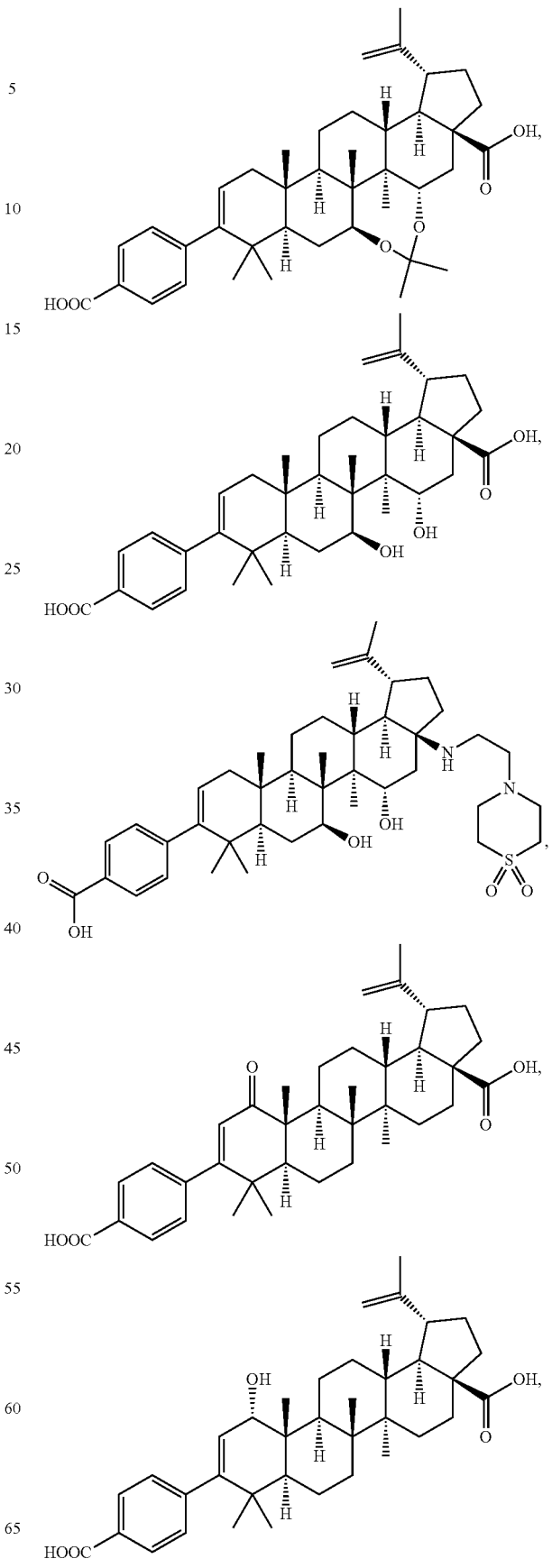

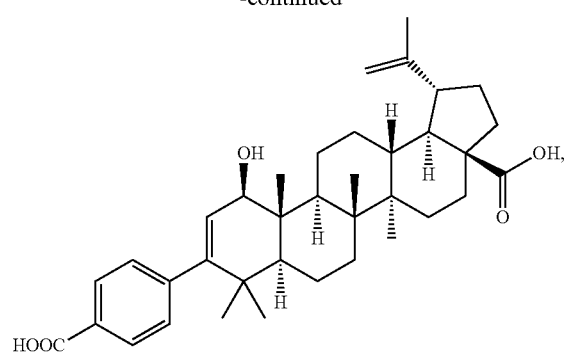
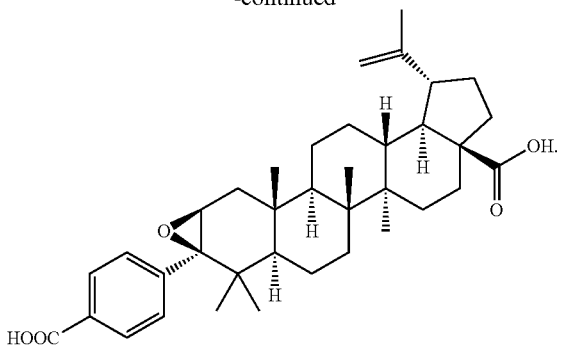
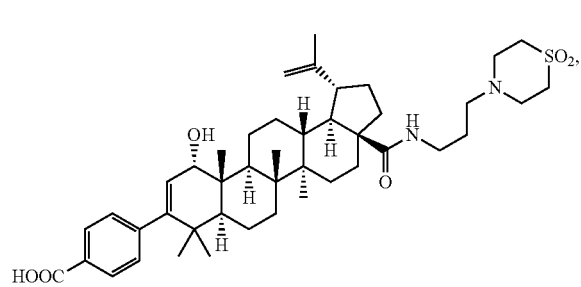
16. A compound, including pharmaceutically acceptable salts thereof, which is selected from the group of:
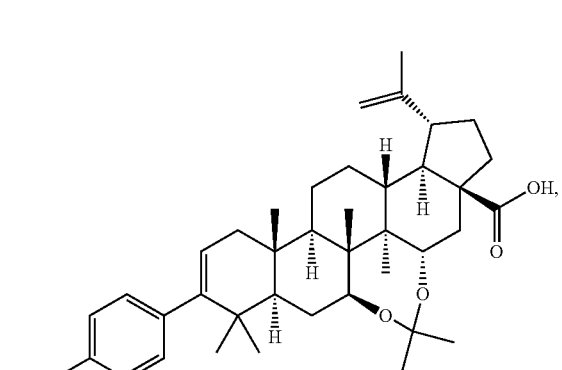
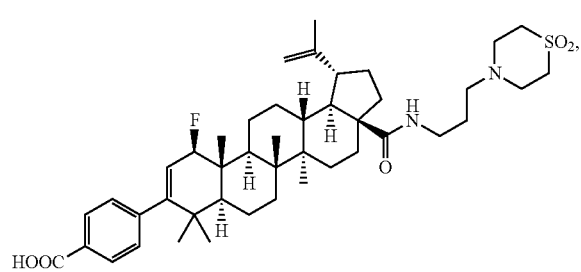
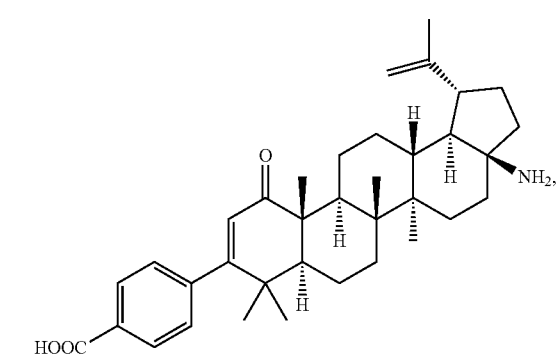
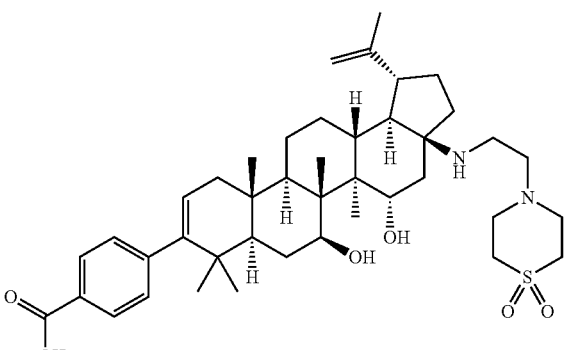
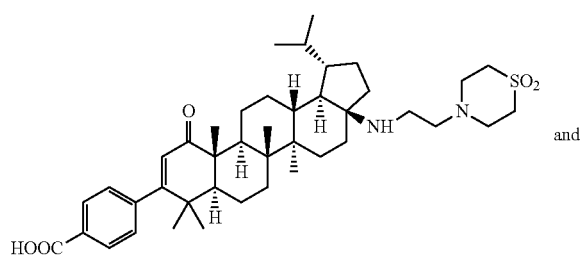
and
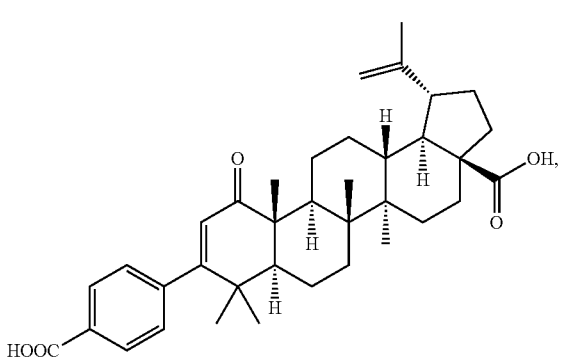

81

-continued

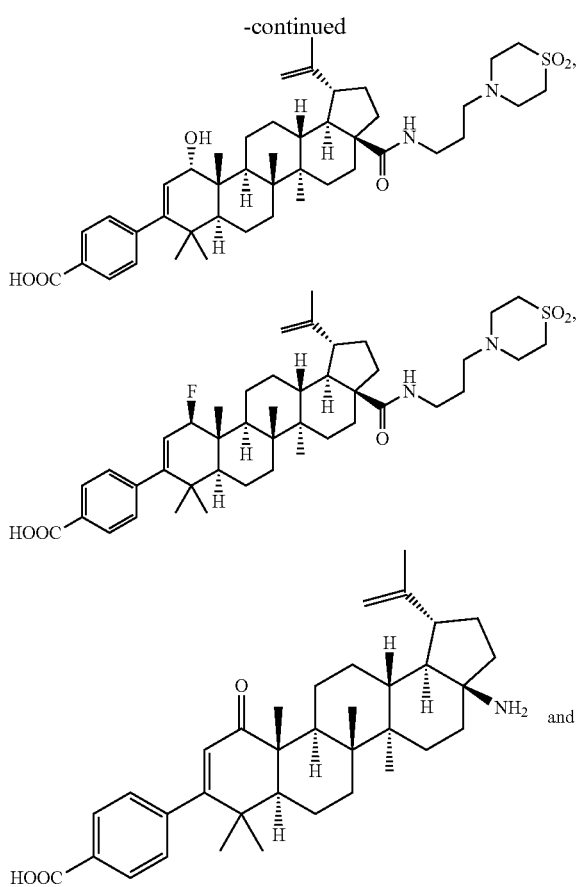

82

-continued

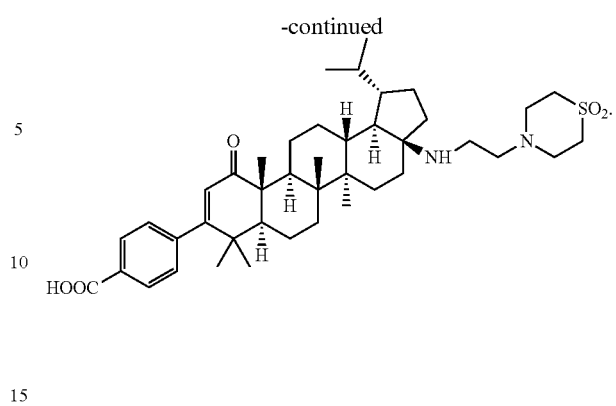

and

17. A composition which comprises one or more compounds as claimed in claim 1, together with one or more pharmaceutically acceptable carriers, excipients, and/or diluents.

18. A composition which comprises one or more compounds as claimed in claim 15, together with one or more pharmaceutically acceptable carriers, excipients, and/or diluents.

19. A composition which comprises one or more compounds as claimed in claim 16, together with one or more pharmaceutically acceptable carriers, excipients, and/or diluents.

* * * * *